United States Patent
Ward et al.

(10) Patent No.: US 7,113,814 B2
(45) Date of Patent: Sep. 26, 2006

(54) TISSUE INTERROGATION SPECTROSCOPY

(75) Inventors: Kevin R. Ward, Glen Allen, VA (US); R. Wayne Barbee, Richmond, VA (US); James Terner, Richmond, VA (US); Rao R. Ivatury, Richmond, VA (US); Fred Hawkridge, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 277 days.

(21) Appl. No.: 10/332,613

(22) PCT Filed: Jul. 13, 2001

(86) PCT No.: PCT/US01/22187

§ 371 (c)(1),
(2), (4) Date: Jul. 29, 2003

(87) PCT Pub. No.: WO02/07585

PCT Pub. Date: Jan. 31, 2002

(65) Prior Publication Data

US 2004/0039269 A1     Feb. 26, 2004

Related U.S. Application Data

(60) Provisional application No. 60/218,055, filed on Jul. 13, 2000.

(51) Int. Cl.
*A61B 5/00* (2006.01)

(52) U.S. Cl. ..................................... 600/310; 600/476

(58) Field of Classification Search ................ 600/310, 600/322, 323, 473, 476; 356/301, 303, 317–320; 250/341.1
See application file for complete search history.

(56) References Cited

U.S. PATENT DOCUMENTS 5,769,081 A     6/1998  Alfano et al.
5,991,653 A    11/1999  Richards-Kortum et al.

*Primary Examiner*—Eric F. Winakur
(74) *Attorney, Agent, or Firm*—Whitham, Curtis & Christofferson, PC

(57) ABSTRACT

In an emergency medicine patient, accurate measurement of change or lack thereof from non-shock, non-ischemic, non-inflammation, non-tissue injury, non-immune dysfunction conditions is important and is provided, as practical, real-time approaches for accurately characterizing a patient's condition, using Raman (3) and/or fluorescence (30) spectroscopy with a high degree of accuracy. Measurement times are on the order of seconds. High-accuracy measurement is achieved with Raman spectroscopy interrogation of tissue. Simultaneous interrogation by NADH fluorescence spectroscopy may be used. Measurements may be non-invasive to minimally invasive. Preclinical (ultra-early) states of shock can be detected (5), severity can be determined, effectiveness of various treatments can be determined.

70 Claims, 35 Drawing Sheets

1) Horse Hb ph 8
2) Horse Hb ph 6
3) Difference 2 minus 1

TISSUE INTERROGATION SPECTROSCOPY

This application claims the benefit of Provisional Application No. 60/218,055, filed Jul. 13, 2000.

FIELD OF THE INVENTION

The invention generally relates to emergency medicine, and especially relates to shock states and critical illnesses and disease states.

BACKGROUND OF THE INVENTION

Shock is a complex entity, which traditionally has been defined as a state in which the metabolic demands of tissues are not matched by sufficient delivery of metabolic substrates, with the major substrate being oxygen. This mismatch commonly results from altered states of organ perfusion such as hemorrhage. Shock additionally involves complex inflammatory and immune mediated events which result from, and may further exacerbate, this initial metabolic mismatch. Many of these events play an important role in the development of subsequent multiorgan dysfunction, failure and death, with this latter mode responsible for over 60% of trauma deaths. Haljamae, H., "Cellular metabolic consequences of altered perfusion," in Gutierres, G., Vincent, J., eds., "Update in Intensive Care and Emergency Medicine: Tissue oxygen utilization (Springer Verlag, 1991), pp. 71–86. Despite the complexities of the inflammatory and immune components of trauma and hemorrhage, there is little debate on linking the severity of these events to the severity of initial perfusion deficits and tissue hypoxia. It is therefore essential to recognize and correct perfusion deficits at their earliest possible time. Although this seems intuitive, up to 80% of trauma patients on close monitoring continue to demonstrate evidence of tissue hypoxia secondary to perfusion deficits after what was considered to be complete resuscitation. Abou-Khalil, B., Scalea, T. M., Trooskin, S. Z., Henry, S. M., Hitchcock, R., "Hemodynamic responses to shock in young trauma patients; need for invasive monitoring," Crit. Care Med., 22:633–639 (1994).

Traditional clinical signs of tissue perfusion such as capillary refill, mental status, heart rate, pulse pressure and systemic blood pressure are very gross indicators of tissue perfusion and can only be considered to be of historic interest except at extreme values. Porter, J., Ivatury, R., "In search of optimal end points of resuscitation in trauma patients," J. Trauma, 44:908–914 (1998). Current markers of tissue perfusion include systemic lactate and base deficit measurements; transcutaneous and subcutaneous gas measurements, gastric and sublingual tonometry and spectroscopic techniques such as NIR absorption spectroscopy, fluorescence quenching, and orthogonal polarization spectral imaging. While these techniques have respective advantages, each is plagued by the relative singularity of its measure, lack of tissue specificity, inability to quantitate, or inability to easily apply or adapt for field use. Identification of any other useful markers is an important objective, and the search continues for further markers of shock states and the like. Effectively measuring and working with both known markers as well as markers being discovered would be highly beneficial to emergency medicine but is not provided in conventional technology. Information about biochemistry in shock states and disease states has not yet fully found its way and been used in practical applications. Rather, currently emergency medicine is left to rely on physical examination not much advanced by conventional, relatively limited spectroscopic measurement technology.

That is, much still turns on observation of simple vital signs. Yet, the diagnosis of shock and its severity can be difficult, and cannot be accomplished with certainty, from simple vital signs. A physical exam, including vital signs, is inadequate in detecting states of uncompensated shock. Ward, K. R., Ivatury, R. R., Barbee, R. W., "Endpoints of resuscitation for the victim of trauma," J. Intensive Care Med., 16:55–75 (2001). Dysoxia can be present despite normal vital signs. Ward et al., id.; Abou-Khalil, B., Scalea, T. M., Trooskin, S. Z., Henry, S. M., Hitchock, R., "Hemodynamic response to shock in young trauma patients: need for invasive monitoring," Crit Care Med. 22(4):633–9 (1994); Scalea, T. M., Maltz, S., Yelon, J., Trooskin, S. Z., Duncan, A. O, Scalafani, S. J., "Resuscitation of multiple trauma and head injury: role of crystalloid fluids and inotropes," Crit Care Med. 22(10):1610–5 (1994); Ivatury, R. R., Simon, R. J., Havriliak, D., Garcia, C., Greebarg, J., Stahl, W. M., "Gastric mucosal pH and oxygen delivery and oxygen consumption indices in the assessment of adequacy of resuscitation after trauma: a prospsective, randomized study," J. Trauma, 39(1):128–34; discussion 34–6 (1995).

In addition, resuscitation of victims of uncompensated shock back to "normal" vital signs is inadequate as a resuscitation endpoint. Unrecognized continued accumulation of additional oxygen debt is still possible and may contribute to later development of multisystem organ failure and death. Shoemaker, W. C., Appel, P. L., Kram, H. B., "Tissue oxygen debt as a determinant of lethal and nonlethal postoperative organ failure," Crit. Care Med., 16(11):1117–20 (1988).

Adding, to a physical exam, global measures of oxygen transport still does not ensure detection of early shock states or provide adequate information to act as sole end-points of resuscitation once shock is recognized and therapy instituted. For an outline of all of the current major technologies that have been used to detect the presence of shock and to guide its treatment, see Ward, Ivatury et al., supra. For various reasons, all have been problematic.

To better understand the difficulties in detecting shock states it is helpful to examine the biphasic relationship between oxygen delivery ($DO_2$) and consumption ($VO_2$) to understand the potential inadequacies of currently available monitoring systems. FIG. 1 demonstrates that $VO_2$ can remain constant over a wide range of $DO_2$. This is possible because cells have the ability to increase their extraction of oxygen (OER) in the face of decreased delivery. This is generally reflected by lower hemoglobin oxygen saturations in blood leaving the organ system ($SvO_2$), which may change before it is apparent in the physical exam. Scalea, T. M., Hartnett, R. W., Duncan, A. O., Atrweh, N. A., Phillips, T. F., Sclafani, S. J., et al., "Central venous oxygen saturation: a useful clinical tool in trauma patients," J. Trauma, 30(12):1539–43 (1990); McKinley, B. A., Marvin R. G., Cocanour, C. S., Moore, F. A., "Tissue hemoglobin O2 saturation during resuscitation of traumatic shock monitored using near infrared spectrometry," J. Trauma, 48(4):637–42 (2000). However, there is a point at which OER cannot keep pace with reductions in delivery. At this point $VO_2$ of the cell or organ falls (critical oxygen delivery: $DO_2crit$) and cells become dysoxic. This results in an increase in the oxidation-reduction (redox) value of the cell, effectively blocking the flow of electrons through the NADH-cytochrome a, a3 cascade in the mitochondria which prevents the formation of ATP. Cytochrome a,a3 (cytochrome oxidase) is the terminal electron acceptor in the mitochondrial electron transport chain. Dysoxia can be recognized by the accumulation of a number of metabolic products such as lactate and intracellular reduced nicotinamide adenine dinucleotide (NADH). NADH offers one of the main sources of energy transfer from the TCA cycle to the respiratory chain in the mitochondria. NADH is situated on the high-energy site of the respiratory chain and during tissue dysoxia it accumulates because less NADH is oxidized to NAD+. The redox state of the mitochondria (NADH/NAD+) therefore reflects the mitochondrial energy state, which in turn is determined by the balance of oxygen availability in the cell and the metabolic rate of the cell. Siegemund, M., van Bommel, J., Ince, C., "Assessment of regional tissue oxygenation," Intensive Care Med., 25(10):1044–60 (1999). Conventional monitoring and measuring used in emergency medicine do not adequately take into account such biochemistry of shock states and the like. Knowing the biochemistry of shock states and the like but not being able to measure and monitor pertinent information thereto has been a frustrating, unresolved problem in emergency medicine.

Conventionally, a primary means of assessing tissue perfusion is through infrared (IR) or near-infrared (NIR) spectroscopy. Human skin and tissue are semi-transparent to wavelengths in this range. However, problems with IR technology arise because water strongly absorbs IR radiation. While NIR absorption spectroscopy does not suffer from water absorption as does classical IR, and NIR absorption spectroscopy is useful for the relative quantification of several specific chromophores such as hemoglobin, myoglobin, and cytochrome oxidase. Nakamoto, K., Czernuszewicz, W. S., "Infrared Spectroscopy," in: *Methods in Enzymology*, 226:259–289 (1993); Piantadisu, C., Parsons, W., Griebel, "Application of NIR Spectroscopy to problems of tissue oxygenation," in Gutierres, G., Vincent, J., eds., *Update in Intensive Care and Emergency Medicine: Tissue oxygen utilization* (Springer Verlag, 1991) pp. 41–44. Other recent work reports the ability of using NIR absorption shift of hemoglobin to measure pH. However, disadvantageously, NIR signals are so broad as to not be well-suited to quantification of overlapping species. Examples of NIR absorption spectroscopy signals being too broad to lend themselves to quantification of overlapping species include the spectra for oxy and deoxy hemoglobin and cytochrome oxidase (see FIG. 2). Owen-Reece, H., Smith, M., Elwell, C. E., Goldstone, J. C., "Near infrared spectroscopy," Br J Anaesth, 82(3): 418–26 (1999). FIG. 2 is a graph of typical broad signals of oxy and deoxy hemoglobin and cytochrome oxidase obtained by NIR absorption spectroscopy. (In FIG. 2, the $HbO_2$ and Hb signals also would include those from myoglobin.)

Conventional NADH-fluorescence techniques are more specific and quantitative than classical NIR absorption spectra but can only measure a single marker. The technique has relied on use of excitation wavelengths in the carcinogenic UV region and has not been reduced to clinical practice. Conventional noninvasive or minimally invasive measures of tissue perfusion include transcutaneous and tonometric (gastric or sublingual) monitoring of various gases such as oxygen and carbon dioxide. The major limitations of these devices are that they are limited to monitoring those specific gases and cannot provide additional information that, if provided, could be useful in diagnosis and stratification of patients. Methods such as tonometry can be cumbersome due to its invasive nature. These methods are also prone to deviations through changes either in minute ventilation or inspired oxygen concentration. Transcutaneous gas monitoring, gastric tonometry, and even sublingual tonometry are one-dimensional and are prone to non-flow related changes caused by hypo or hyper ventilation. Also, with the exception of sublingual tonometry, application of these methods in the field is problematic. Weil, M., Nakagawa, Y., Tang, W., et al., "Sublingual capnometry: A new noninvasive measurement for diagnosis and quantification of severity of circulatory shock," Crit. Care Med., 27:1225–1229 (1999).

Another concern associated with measurement of shock states, and balanced with other factors relating to measurement, is invasiveness. NIR absorption spectroscopy is being aggressively studied to use signals from these chromophores to noninvasively monitor oxygen transport at the tissue level. McKinley et al., supra. Perhaps the best-known use of this technology is in the monitoring of cerebral hemodynamics. The basis for this is that the majority of blood volume in an organ is venous and thus the tissue hemoglobin saturation should reflect the state of oxygen consumption of the tissue. Again, broad overlap of signals in addition to needing to know the pathlength of light presents challenges in quantification and differentiation of signals. For example it is difficult to distinguish hemoglobin and myoglobin making NIR use in hemorrhage problematic since myoglobin has a p50 of only 5 mmHg. Gayeski, T. E., Honig, C. R., "Direct measurement of intracellular O2 gradients; role of convection and myoglobin," Adv Exp Med Biol, 159:613–21 (1983). Because soft tissue and bone are translucent to NIR light, NIR can penetrate to significant depths, a feature with both advantages and disadvantages. Monitoring the redox state of cytochrome oxidase is also difficult unless baseline absorptions are known. There is also significant overlap between the cytochrome oxidase and hemoglobin signals. Despite this, NIR measurements of tissue saturation ($StO_2$) are being marketed.

Although some manufacturers of NIR absorption spectroscopy equipment claim to differentiate between the two species of oxygen hemoglobin and myoglobin, no work to this effect exists in the medical literature. In fact, evidence exists that a major portion of the NIR absorption spectroscopy signal reported from hemoglobin actually originates from myoglobin.

Another problem for NIR is that in terms of use on hollow organ systems such as the stomach, data from NIR absorption spectroscopy would likely include signals from non-stomach organs and thus not reflect data from the mucosal surface of the stomach.

Surface NADH fluorescence has been used to detect cellular dysoxia in a number of organ systems. Siegemund et al., supra. The traditional technique uses unique excitation light sources and detection filters to take advantage of the fact that NADH will fluoresce (emit light at 460 nm) when excited at a wavelength of 360 nm (near-UV). This technique has been used in video microscopy/fluorometry experiments. Van der Laan, L., Coremans, A., Ince, C., Bruining, H. A., "NADH videofluorimetry to monitor the energy state of skeletal muscle in vivo," J. Surg. Res., 74(2):155–60 (1998). However, such conventional methods do not necessarily provide optimum resolution.

Adverse effects of certain compounds (such as vasopressin and norepinephrine) on oxygen transport and the immune/inflammatory response are now beginning to be appreciated with manipulation of their actions being studied as therapeutic strategies. Kincaid, E. H., Miller, P. R., Meredith, J. W., Chang, M. C., "Enalaprilat improves gut perfusion in critically injured patients," Shock, 9(2):79–83 (1998); Catania, R. A., Chaudry, I. H., "Immunological consequences of trauma and shock," Ann. Acad. Med. Singapore, 28(1):120–32 (1999). However, satisfactory measurement of such compounds in vivo without invasive probing has not yet been provided.

Thus, current technology includes pulmonary artery catheters, repetitive measures of lactate and base deficit, splanchnic tonometry, sublingual tonometry, NIR absorption spectroscopy, transcutaneous gas monitoring, phosphorescence quenching and fluorescence technology (indwelling blood gas/pH catheters). No such technology is without a substantial disadvantage. Civilian prehospital emergency medical services systems, emergency physicians, trauma surgeons, intensive care physicians, cardiologists, anethesiologists, and military medical personnel continue to be plagued by the insensitivity of the physical exam, lack of readily available physiologic and metabolic markers to judge the presence and severity of shock states, and lack of real-time relevant measurement approaches. In addition, it has been difficult to use singular measures to guide treatment or predict outcome. These problems are greatly magnified as the scale of the wounded population increases (such as on the battlefield and the various pre-definitive echelons of care provided to wounded soldiers or in a natural disaster). To the inventors' knowledge, currently no conventional techniques are available for real-time monitoring of a broad range of potentially valuable emergency medicine markers of shock, tissue ischemia, tissue injury, tissue inflammation, or tissue immune dysfunction.

SUMMARY OF THE INVENTION

The invention realizes methods, profiles, medical measurement devices, and other products for accurate measurement of change or lack thereof from non-shock, non-ischemic, non-inflammation, non-tissue injury, non-immune dysfunction conditions which are referred to herein as "baseline conditions". In attention to advantageous accuracy in such measurement, the invention provides practical, real-time approaches for accurately characterizing a patient's condition with respect to baseline conditions. With Raman and/or fluorescence spectroscopy according to the invention, change from baseline conditions is measured, characterized, monitored, identified and/or followed with a high degree of accuracy with measurement times on the order of seconds. Such high-accuracy measurement is achieved with Raman spectroscopy (such as resonance Raman spectroscopy) interrogation of tissue, optionally with simultaneous interrogation by fluorescence spectroscopy of compounds such as NADH. The tissue interrogation advantageously may be non-invasive to minimally-invasive to totally invasive. With methods and products according to the present invention, advantageously preclinical (ultra-early) states of shock, tissue ischemia, tissue injury, and tissue inflammation can be detected, severity can be determined, and the effectiveness of various treatments aimed at resolving the shock state can be determined, and other beneficial effects for patient care can be achieved.

In order to accomplish these and other objects of the invention, the present invention in a preferred embodiment provides a tissue analysis method, comprising interrogating a biological material (such as a biological tissue or a bodily fluid) with Raman spectroscopy and fluorescence spectroscopy to obtain spectroscopy results.

In another preferred embodiment, the invention provides a method of diagnosing shock, tissue ischemia, tissue inflammation, or tissue immune dysfunction, comprising: (A) for a target molecule population, taking a sample Raman spectroscopy, and/or fluorescence spectroscopy, profile for a patient; (B) comparing the sample spectroscopy profile with a pre-established Raman spectroscopy and/or fluorescence spectroscopy profile for the target molecule population under baseline conditions.

A further preferred embodiment provides a spectroscopy comparative profile, comprising: a pre-established Raman spectroscopy and fluorescence spectroscopy profile for a target molecule population under baseline conditions; and a sample Raman spectroscopy and fluorescence spectroscopy profile for the target molecule population.

The invention also provides for a preferred embodiment which is a method of diagnosing abnormalities in vivo and in situ, comprising: (A) for a target molecule population, taking a sample Raman spectroscopy and/or fluorescence spectroscopy profile for a patient; (B) comparing the sample Raman spectroscopy or fluorescence spectroscopy profile with a pre-established Raman spectroscopy or fluorescence spectroscopy profile for the target molecule population under baseline conditions; and (C) using differences identified in said comparing step to identify an abnormality.

In a particularly preferred embodiment of the inventive methods, simultaneous fluorescence spectroscopy probing of NADH and resonance Raman spectroscopy are performed.

Another preferred embodiment of the invention provides a medical measurement device comprising: a spectrometer with multiple wavelength settings for resonance Raman spectroscopy; and a biological probe electrically connected to the spectrometer.

Additionally, the invention in another preferred embodiment provides a spectroscopy comparative profile, comprising: a pair of Raman spectroscopy or fluorescence spectroscopy profiles for a target molecule population, wherein one profile was taken from a patient after a medical event concerning the patient.

A further preferred embodiment of the invention provides a computer system comprising: a database of stored baseline Raman spectroscopy and/or fluorescence spectroscopy profiles and a means to store patient Raman spectroscopy and/or fluorescence spectroscopy profiles.

BRIEF DESCRIPTION OF THE DRAWINGS

The foregoing and other objects, aspects and advantages will be better understood from the following detailed description of the preferred embodiments of the invention with reference to the drawings, in which:

FIG. 22($b$) are preliminary Raman spectra of the high energy phosphates ATP and ADP. FIG. 22($c$) are preliminary Raman spectra of the glycolytic end-products pyruvate and lactate, along with the excitatory amino acid and neurotoxin glutamate. FIG. 22($d$) are preliminary Raman spectra of the oxygen transporters hemoglobin (Hb) and myoglobin (Mb), from an equine. FIG. 22($e$) includes preliminary Raman scans of uncooked beef, with the top scan taken in a darker area, and the bottom scan taken in a lighter area with more saturated myoglobin.

FIG. 26($e$) is a top view of a fiber optic bundle shown schematically in FIGS. 26($b$), 26($c$) and 26($d$).

DETAILED DESCRIPTION OF THE PREFERRED EMBODIMENTS OF THE INVENTION

Figure 1:
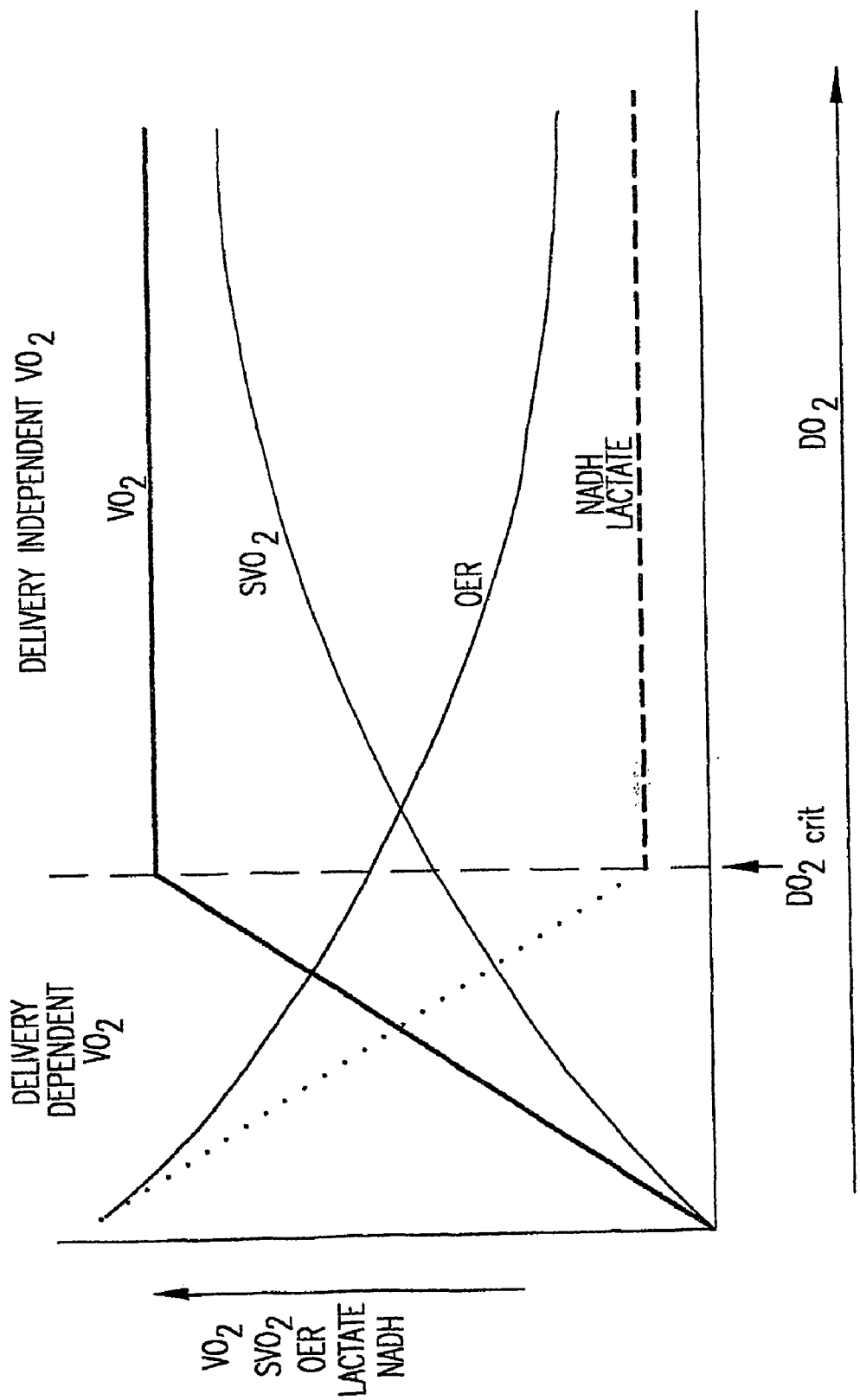
FIG. 1 is a traditional biphasic oxygen delivery and consumption curve.

The present invention provides methods and products in which resonance Raman spectroscopy interrogates biological material (such as tissue or a bodily fluid) at near-UV excitation. The Raman spectroscopy may proceed with or without simultaneous fluorescence spectroscopy (such as NADH fluorescence spectroscopy). The interrogation advantageously may be in a non-invasive to minimally-invasive manner, but is not required to be so and if desired may be invasive. Data from interrogating tissue according to the invention may be used to detect preclinical (ultra-early) states of shock and other tissue injury and disease states, determine severity, and determine the effectiveness of various treatments aimed at resolving the shock or tissue disease/injury state of a patient.

In a preferred embodiment of the invention, a tissue analysis method comprises interrogating a biological tissue with Raman spectroscopy and fluorescence spectroscopy to obtain spectroscopy results. The Raman spectroscopy used in the present invention is that based on the Raman effect, which has been known for over 70 years and is caused by absorption of light leading to the transition of a molecule from the ground state to an excited state, followed by the emission of light with a different wavelength. Raman, C. V., Krishnan, K. S., "The colour of the sea," Nature (London), 121:619 (1928). The Raman effect has only recently, through the advancements and miniaturization of fiber optic, laser, and detector technology, become a practical technique for clinical use. Because each molecular species has its own characteristic molecular vibrations, a Raman spectrum provides a unique "fingerprint" useful for sample or marker identification. Hanlon, E. B., Manoharan, R., Koo, T. W., Shafer, K. E., Motz, J. T., Fitzmaurice, M., et al., "Prospects for in vivo Raman spectroscopy," Phys Med Biol, 45(2): R1–59 (2000); Diem, M., "Introduction to modern vibrational spectroscopy," New York: Wiley (1993). While any wavelength of light theoretically can be used as an excitation source to provide a Raman spectrum, visible excitation can produce strong broadband fluorescence, which undesirably can overwhelm Raman signals. Nevertheless, wavelengths can be chosen that produce resonance due to matching of the excitation wavelength and the electronic energy state of the scattering molecule. While Raman scattering is a rather low energy phenomenon requiring sensitive detectors, the signal is greatly enhanced when the molecule of interest is resonant (absorption maximum near the laser wavelength). This signal enhancement at a resonant frequency may be referred to as "resonance Raman spectroscopy" and allows for the selective detection of individual species of very low concentration within a complex mixture. Hanlon et al., supra.

If the excitation wavelength does not induce fluorescence within the wavelength region of interest, then remarkably high resolution Raman spectra can be obtained. If fluorescence does occur, this can be reduced or even eliminated in many instances by tuning of the excitation wavelength. Thus, while interfering fluorescence may occur with a particular excitation wavelength, it may not occur within the UV or NIR range where one could detect signals either above or below the fluorescing region, as the case may be. Hanlon, E. B., Manoharan, R., Koo, T. W., Shafer, K. E., Motz, J. T., Fitzmauric, M., Kramer, J. R., Itzkan, I, Dasari, R. R, and Feld, M. S., "Prospects for in vivo Raman spectroscopy," Phys. Med. Biol.; 45: R1–R59 (2000).

In the invention, the wavelengths for the Raman spectroscopy and/or fluorescence spectroscopy are wavelengths for which such spectroscopy equipment may be set, suitably for interrogating biological tissue in a living patient. Preferably resonance Raman spectroscopy according to the invention is performed at a deep ultraviolet wavelength, i.e., at 390 to 420 nm. Modifications of Raman spectroscopy that can be applied include Fourier Transform Raman Spectroscopy, Nonlinear Raman Spectroscopy, Raman difference spectroscopy, and Raman Optical Activity.

Examples of Raman spectra are FIGS. 3, 4, 5, 6, 7, 8, 9, 10, 11, 12, 13, 22($a$)–($e$), 23, 24, 25. Examples of NADH fluorescence spectra are FIGS. 14, 15, 16, 17, 18, 19, 20, 21.

The inventive methods, products and profiles may include signal enhancement at a resonant frequency for a target molecule of the target molecule population. The inventive methods may include operating an electromagnetic radiation generator at a range of selectable wavelengths from about 270 nm to about 20,000 nm. Spectroscopy may be performed for multiple wavelengths. Preferably the Raman spectroscopy is resonance Raman spectroscopy at 390 to 420 nm wavelength. Because basic Raman scattering is a rather low intensity phenomenon requiring sensitive detectors, preferably Resonance Raman Spectroscopy (RRS) techniques are used, to enhance the signal when the molecule of interest is resonant (absorption maximum near the laser wavelength). The signal strength of Raman can be boosted by several orders of magnitude by providing areas of resonance. Also, use of resonant wavelengths will allow limiting laser power density to a minimum (well below the skin damage threshold of 4 watts/cm$^2$). Fluorescence can be avoided by choosing wavelengths not prone to this phenomenon, and through fluorescence quenching. Conversely, fluorescence may be advantageously used for quantification if a particular target is found to have identifiable Raman spectra in one light range such as the NIR but fluoresces at another light range such as the UV. Use of near UV wavelengths (violet, ~406 nm) will avoid the mutagenic potential of UV radiation, while insuring a strong Raman signal.

Figure 2:
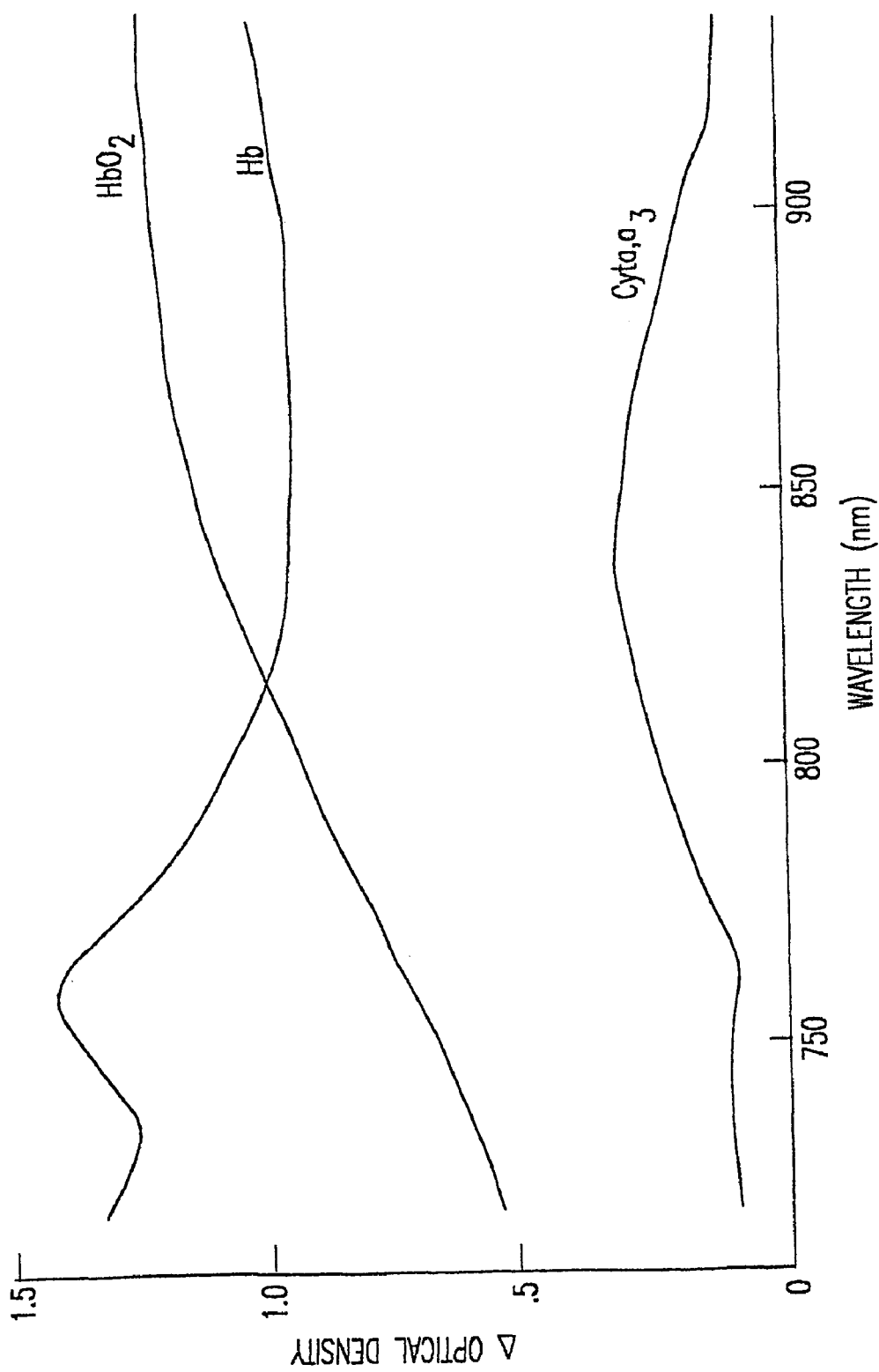
FIG. 2 is a graph of oxy and deoxy hemoglobin and cytochrome oxidase obtained by NIR absorption spectroscopy, with Δoptical density plotted versus wavelength (nm).
Figure 3:
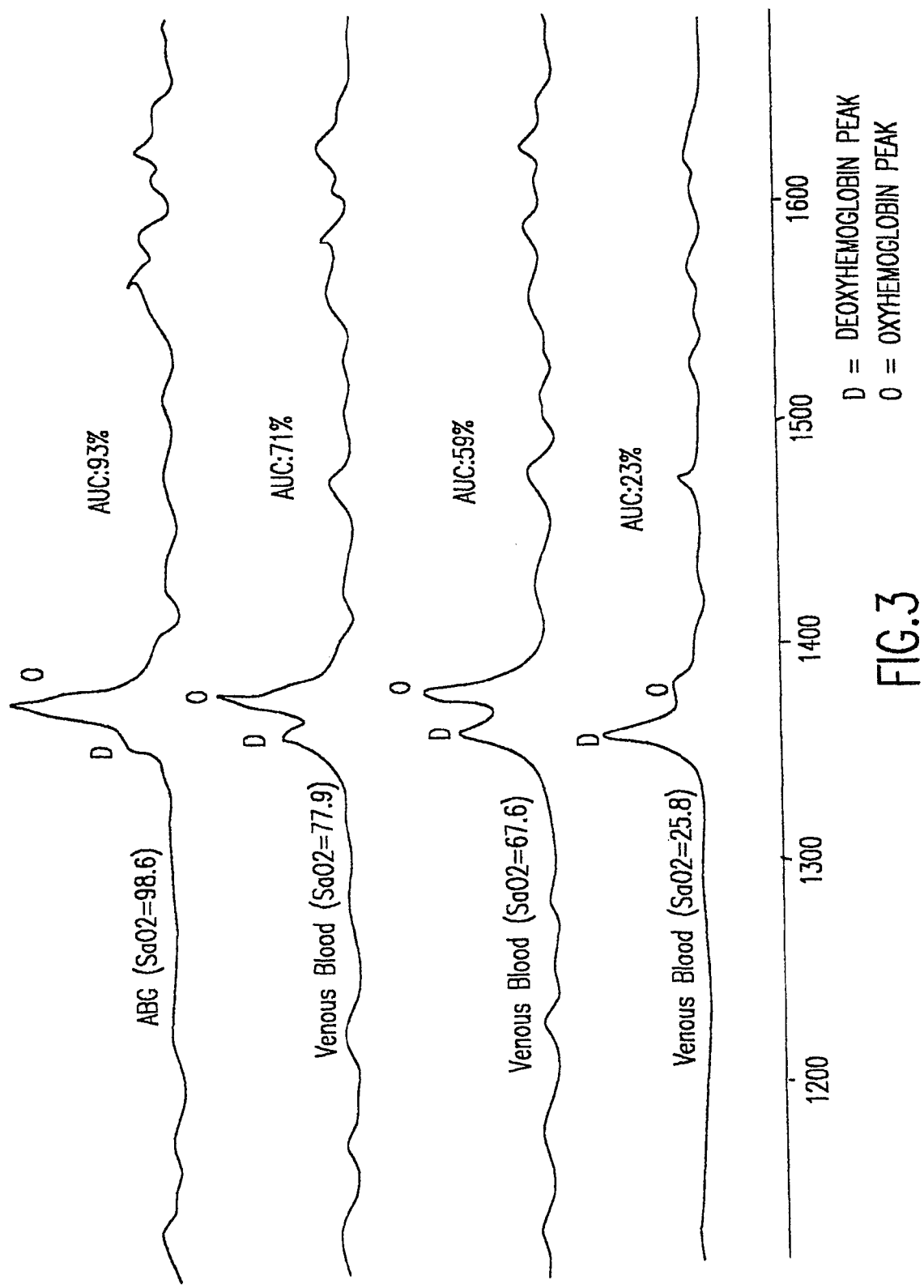
FIG. 3 shows near-UV resonance Raman spectroscopy according to the invention for human blood at various oxygen saturation levels.
Figure 4:
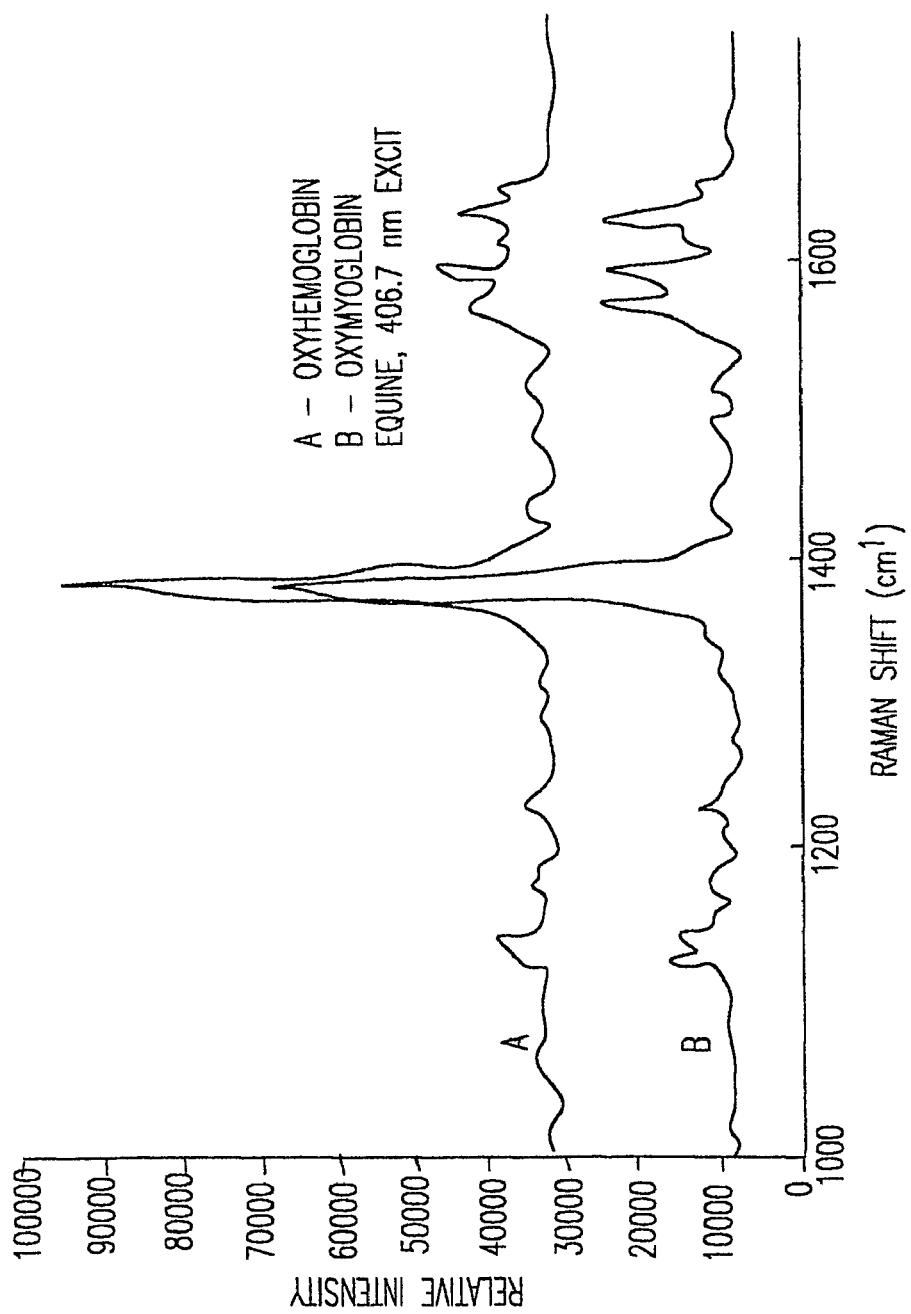
FIG. 4 shows resonance Raman spectroscopy according to the invention of both oxygen hemoglobin and myoglobin.

The use of Raman spectroscopy in the near-UV range within the clinical settings according to the invention has several advantages with respect to other optical techniques such as IR and NIR absorption spectroscopy. Use of resonance Raman spectroscopy in the near-UV range (406.7 nm) may overcome many problems associated with NIR absorbance spectroscopy and other markers of tissue perfusion. Raman spectroscopy in the NIR takes advantage of the remark transparency of tissue at these wavelengths, while at the same time providing high-resolution vibrational signals. Spiro, T. G., "Resonance Raman spectroscopy: A new structure probe for biological chromophores," Accts. Chem. Res., 7:339–344 (1974); Terner, J., El-Saye, M. A., "Time-resolved resonance Raman spectroscopy of photobiological and photochemical systems," Accts. Chem. Res., 18:331–338 (1985). Hemoglobin has strong absorption and resonance properties in the near-UV range. FIG. 3 depicts data from human blood samples in the laboratory demonstrating the sharp peaks of oxy and deoxy human hemoglobin samples. (The area under the curve (AUC) in FIG. 3 of the Raman spectra produce oxygen saturations comparable to that from a multiwavelength co-oximeter.) Comparison of area under the curves of the oxy-peak and blood gas saturations yielded a correlation coefficient of 0.997. These sharp peaks should be compared to the broad overlapping peaks of oxy and deoxy hemoglobin obtained by NIR absorption spectroscopy in FIG. 2. Furthermore, the resonance Raman effect for hemoglobin is so specific that it can be differentiated from the resonance Raman effect of myoglobin (see FIG. 4). FIG. 4 shows resonance Raman spectroscopy of both oxygen hemoglobin and myoglobin, demonstrating an ability to distinguish between the two.

Analyzing the spectroscopy data by computing the AUC has been mentioned. Alternately to computing area, peak height analysis may be performed. For example, tissue hemoglobin oxgyen saturation ($StO_2$) may be determined by either comparing area under the curve of the spectra for both oxyhemoglobin and deoxyhemoglobin and/or comparison of the peak heights between the two species. Each computation provides a percentage. The latter technique is likely to be preferable.

A characteristic of near-UV light is that it can only penetrate tissue to a depth of 1–2 mm and is noncarcinogenic. Although at first thought, depth of penetration might seem to be a disadvantage, actually there is not such a disadvantage. Pathlength becomes less important in this case in terms of quantification issue. Probe contact may be unnecessary, and fiber optics may be simplified. In terms of shock states, blood flow to the surface of any organ is compromised first. In terms of use on hollow organ systems such as the stomach, signals from near-UV resonance Raman spectroscopy would be only from the mucosal surface (an advantage over data from NIR absorption spectroscopy which would likely include signals from non-stomach organs and thus not reflect data from the mucosal surface of the stomach.)

While taking the Raman spectroscopy profile and the fluorescence spectroscopy measurement on the patient at the same time is a preferred embodiment, it will be appreciated that in other embodiments the invention does not require using both Raman and fluorescence spectroscopy.

The fluorescence spectroscopy (such as broadband fluorescence spectroscopy) of the present invention, is performed at between 390 and 800 nm. A most preferred example of fluorescence spectroscopy according to the invention is NADH surface-subsurface fluorescence spectroscopy.

As examples of the biological tissue according to the invention may be the brain, heart, lung, liver, blood, tongue or other oral mucosa, eye (such as the cornea or retina), the esophagus and stomach, peripheral skeletal muscle, skin, intestines, pancreas, kidney, bladder, urethra, skin, nailbed, cervix, uterus, oropharynx, nasopharynx, esophagus, blood etc. Probing on the tongue/oral mucosal, skin, or cornea/retina optionally may be totally noninvasive, without the requirement for probe contact with tissue. For probing the esophagus or stomach, simple fiber optics are constructed into a nasogastric tube for measurements at the level of the esophageal or stomach mucosa. Fiber optics also can be used in urinary catheters for monitoring of substances in the urine or for interrogation of the bladder mucosa. Skeletal muscle or dermis can be assessed with fiber optics of a size insertible through small needles, inserted into a muscle belly such as the deltoid or quadriceps.

The inventive methods may include monitoring a specific tissue bed (brain, heart, lung, liver, eye, blood, etc.) in the patient; placing a probe on or near any mucosal or epithelial covered surface of a body or an organ; detecting exhaled markers or mediators of organ injury (such as by placing a detector at the airway of the patient). Examples of exhaled markers or mediators are isoprostanes and/or myeloperoxidase.

Markers also may be present in a biological material according to the present wherein the markers are contained in urine, saliva, wound exudates, vitreous humor, aqueous humor, tissue exudate, gastric contents, fecal matter, or other biological materials.

The interrogating of biological material such as tissue according to the invention may be, but is not required to be, noninvasive. To maximize the number of markers and mediators that can be measured, a minimally invasive approach is preferred. Interrogating may be intermittently or continuously. A preferred example of minimally invasive probing is by minimally invasively probing the patient by a fiber optic probe or probe array inserted into a tissue bed. The tissue may be in vivo and in situ, but is not required to be. Alternately, the tissue may be removed from a patient before the tissue interrogation. As examples of interrogating tissue are mentioned inserting a probe or probe array into a muscle. Preferably interrogation is by a minimally invasive probe approach, with muscle and interstitium being interrogated directly. Such a minimally invasive approach is preferred for several reasons. UV light does not significantly penetrate epidermis. NIR light can penetrate several centimeters of tissue and can thus probe epidermis, dermis, and muscle. The inability to know the path length of light and to separate the signal of myoglobin from hemoglobin make interpretation of data for the noninvasive use of NIR absorption spectroscopy at any site other than the brain to be conventionally difficult, and a drawback to be avoided. The large number of valuable markers, which can be detected in the UV and NIR range by Raman spectroscopy, more than outweigh any drawback to placing a small probe intramuscularly. Bench experiments have allowed measures to be made of such substances as hemoglobin within cells in the UV range. (See J. Terner, T. G. Spiro, M. Nagumo, M. F. Nicol, and M. A. El-Sayed, "Resonance Raman spectroscopy in the picosecond timescale: the CO hemoglobin photo-intermediate," J. Amer. Chem. Soc., 102: 3238–3239 (1980); J. Terner, J. D. Stong, T. G. Spiro, M. Nagumo, M. F. Nicol, and M. A. El-Sayed (1980), "Picosecond resonance Raman spectroscopic evidence for excited state spin conversion in carbonmonoxy-hemoglobin photolysis," Proc. Natl. Acad. Sci. USA, 78: 1313–1317; J. Terner, T. G. Spiro, D. F. Voss, C. Paddock and R. B. Miles, "Picosecond resonance Raman spectroscopy of oxyhemoglobin photolysis," J. Phys. Chem., 86: 859–861 (1982)). Such results indicate that cell penetration of the near-UV wavelength in the interstitium will not pose a major problem.

In the inventive methods and products, the obtained spectroscopy results preferably may be for at least one mediator or marker associated with a shock state and/or tissue injury; tissue ischemia, tissue inflammation and/or tissue immune dysfunction; for presence and/or proportions for the at least one shock state and/or tissue injury mediator or marker; for at least one mediator associated with a shock state and/or tissue injury or tissue ischemia, inflammation or immune dysfunction and/or for at least one marker of tissue perfusion or injury.

A marker and/or mediator according to the present invention may be within intracellular, interstitial or intravascular space or within exhaled air from a patient. The marker and/or mediator may be selected from the group consisting of lactate, pyruvate, ATP, PCr, AMP, ADP, Pi, NAD, NADH, albumin, endotoxin, exotoxin, microbes, cytokines-chemokines, procalcitonin, hormones, myeloperoxidase, elastase, xanthine oxidase, xanthine dehydrogenase, fatty acid binding proteins, catecholamines and vasoactive peptides. The marker or mediator may be a metabolic or pro or anti-inflammatory marker or mediator. Cardiac biomarkers, GI markers, cerebral markers, skin markers, lung markers, blood markers, and/or eye markers, etc. are mentioned as examples.

Examples of spectroscopy results according to the invention may be, e.g., data relating to diagnosing and/or following progression or resolution of shock states and/or tissue injury (such as inflammatory or immune dysfunction), and/or tissue ischemia; determining whether the tissue has insufficient oxygen delivery to meet metabolic demands of the tissue while simultaneously determining whether mitochondrial dysfunction or injury exists; monitoring for appearance of one or more tissue markers specific for a specific disease state; determining tissue viability; diagnosing tissue injury, tissue inflammation or tissue immune dysfunction; and/or continuously interrogating the patient for appearance of abnormal tissue markers specific for a suspected disease state. A preferred example of spectroscopy results are results relating to diagnosing shock.

As examples of spectroscopy results according to the present invention may be given data for tissue hemoglobin oxygen saturation including amount of oxyhemoglobin and deoxyhemoglobin by Raman spectroscopy; data for NADH presence and/or accumulation by fluorescence spectroscopy; data for oxygenated hemoglobin, deoxygenated hemoglobin and/or NADH; data for myoglobin oxygenation saturation; data for cytochrome oxidase redox status; data for pH of the tissue. A most preferred example of spectroscopy results is data for tissue hemoglobin oxygen saturation by Raman spectroscopy combined with data for NADH presence and/or accumulation by fluorescence spectroscopy.

The spectroscopy results according to the invention may be for absolute concentration (such as absolute concentration of hemoglobin in the tissue) or for relative concentration. Examples of relative concentrations are NAD/NADH; lactate/pyruvate; Pcr-ATP; ATP-ADP; Pcr-Pi; oxidized cytochrome oxidase to reduced cytochrome oxidase, and/or oxyhemoglobin with deoxyhemoglobin.

The spectroscopy results according to the invention advantageously are available on the order of seconds. Signal processing and computer algorithms may be used to process the spectroscopy data.

Another preferred embodiment of the invention provides a medical measurement device comprising: a spectrometer with multiple wavelength settings for resonance Raman spectroscopy; and a biological probe electrically connected to the spectrometer. Inventive medical measurement devices optionally may include a fluorescence spectrometer electrically connected to the biological probe; a laser source (such as a laser tunable to multiple wavelengths) and a charge coupled device. By using a laser tunable to multiple wavelengths, multiple target molecules may be detected. Such multiple target molecules may have useful detectable absorption, resonance Raman and fluorescence spectra at differing wavelengths. Exemplary devices according to the invention may be seen with regard to FIG. 26(a)–(e).

Figure 26A:
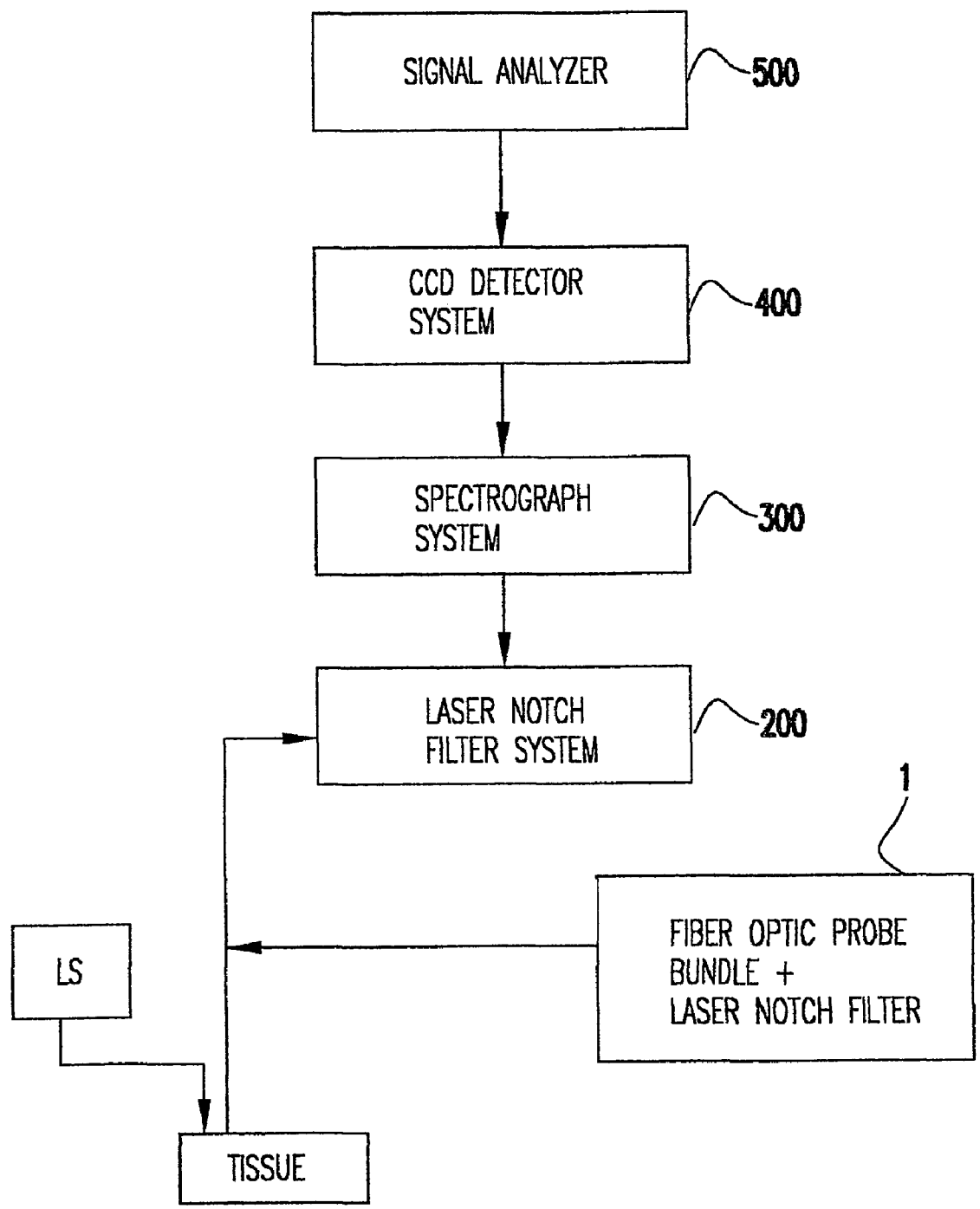
FIGS. 26($a$), 26($b$), 26($c$) and 26($d$) are schematic views of devices according to the invention.
Figure 26B:
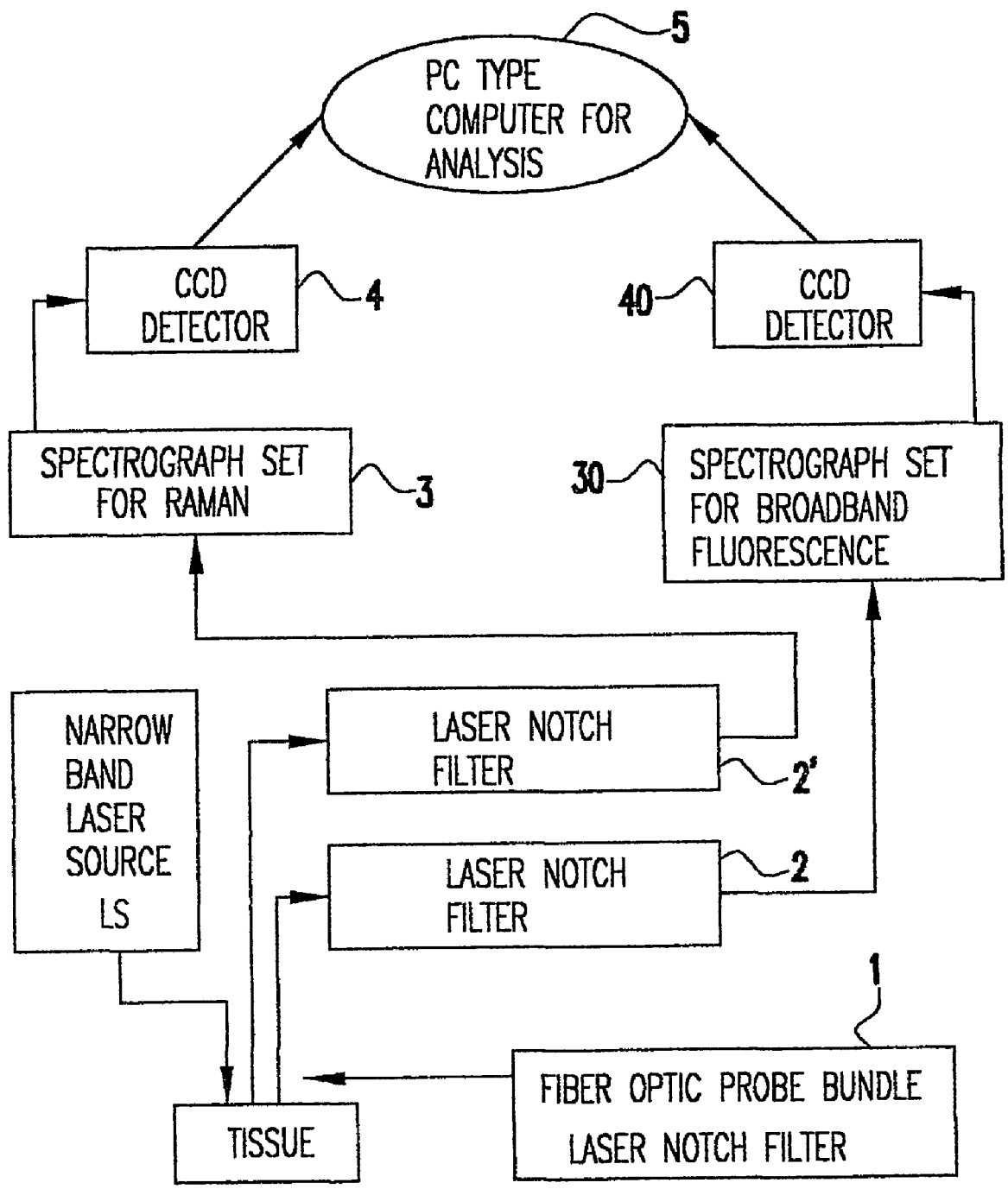
Figure 26C:
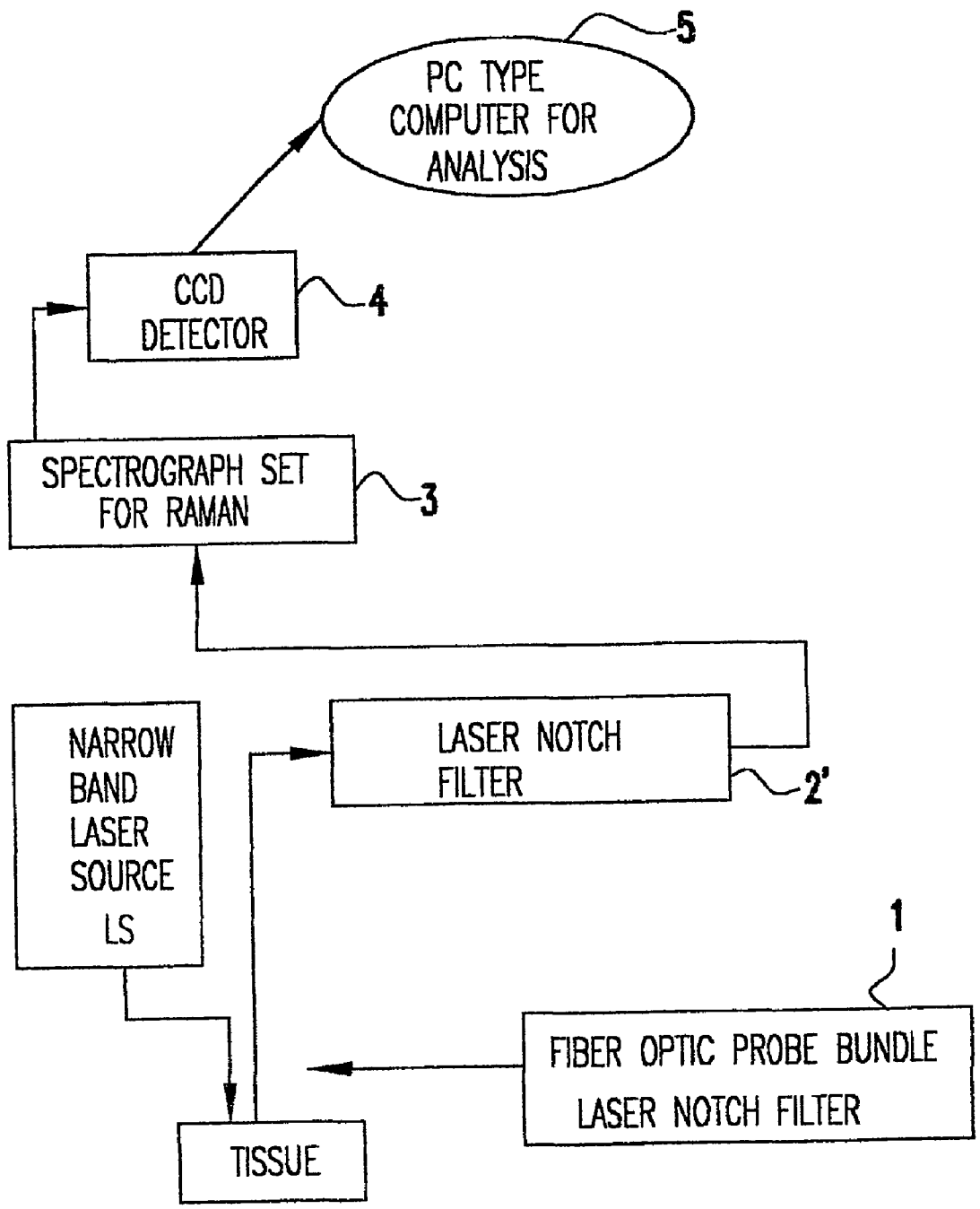
Figure 26D:
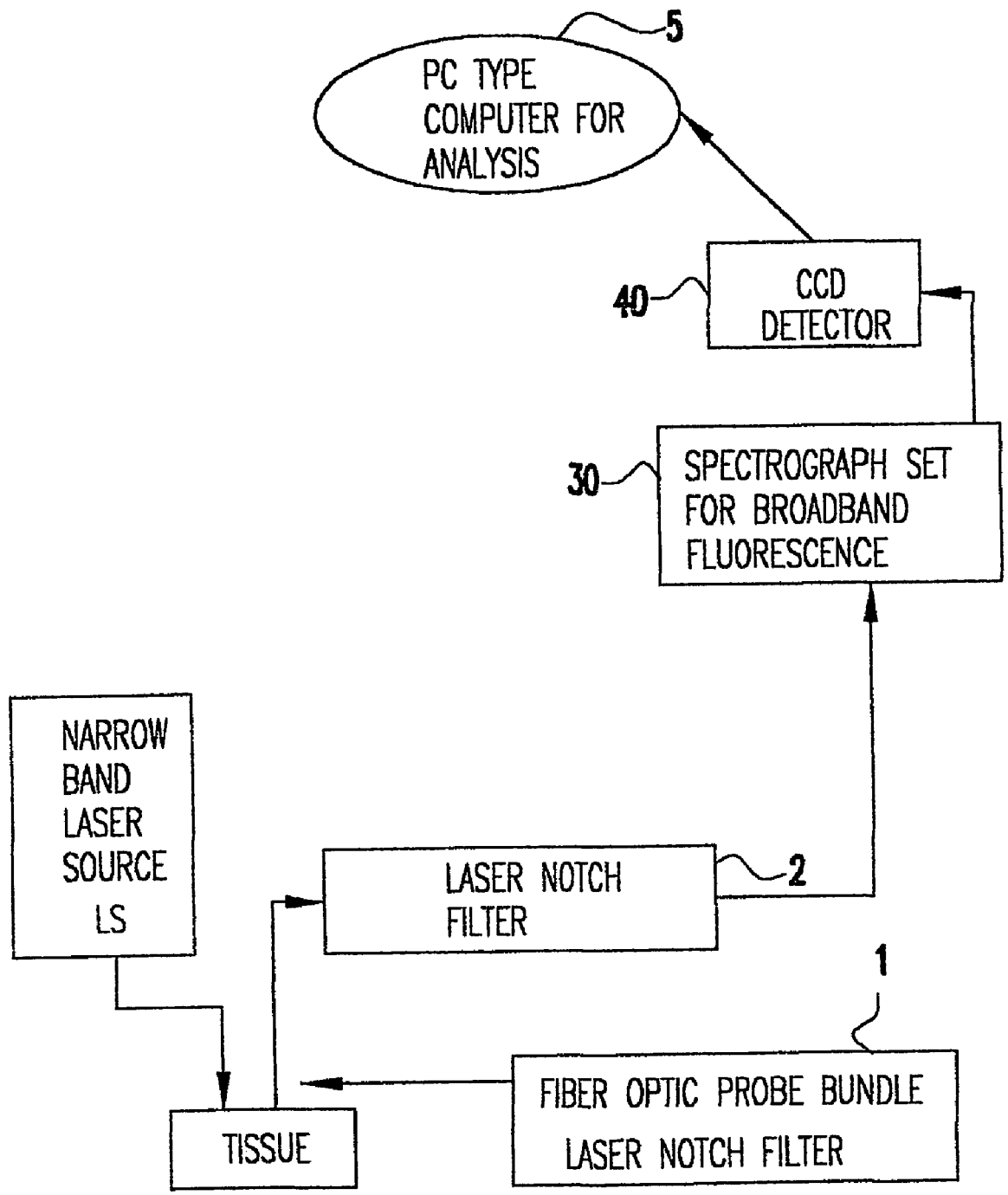
Figure 26E:
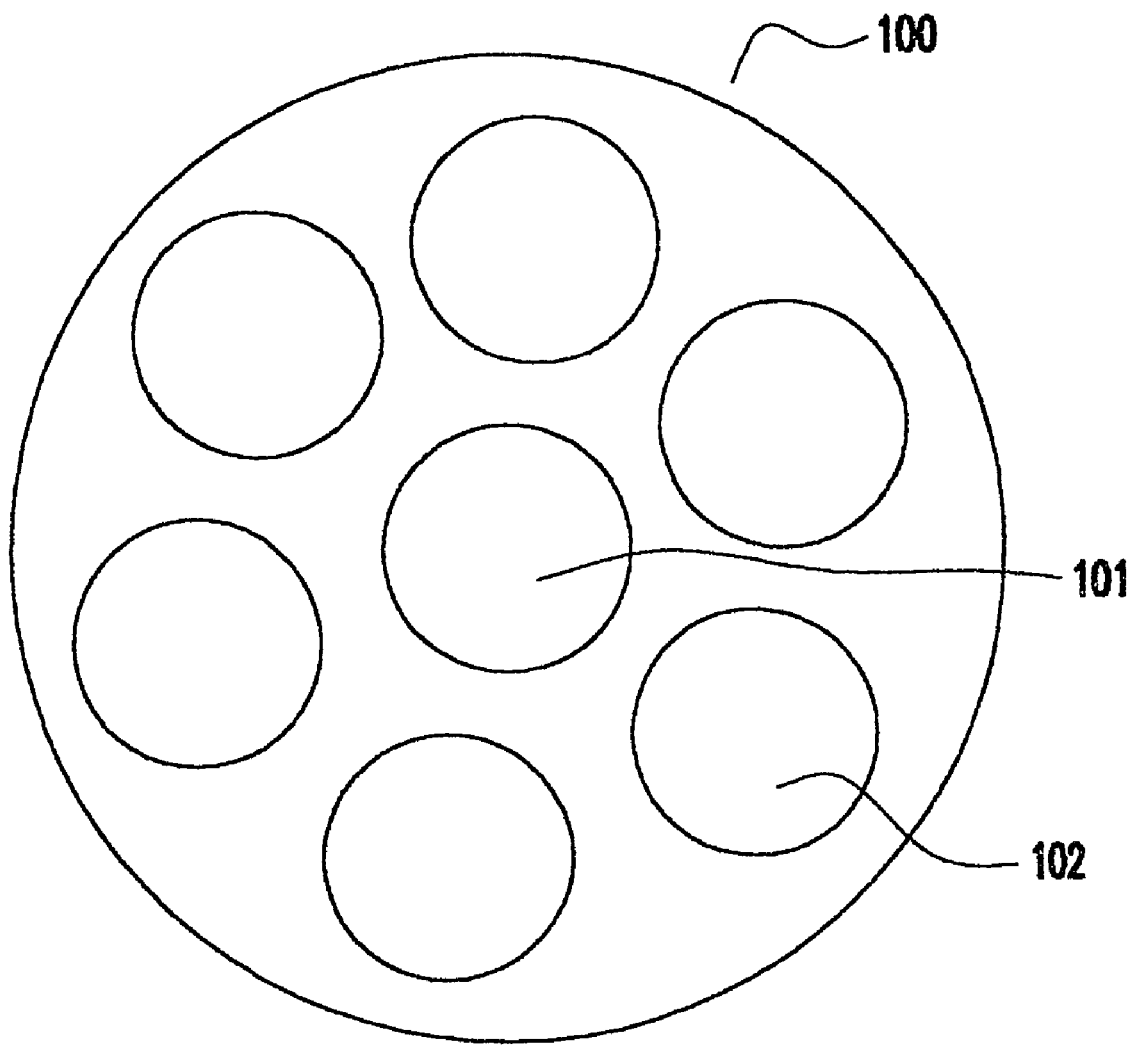

With reference to FIG. 26(a), a fixed frequency laser (preferably such as a laser LS including, but not limited to, wavelengths of approximately 290 to 420 nm) is piped 1 through one leg of a fiber optic bundle. An example of fiber optic bundle 100 is seen in further detail in FIG. 26(e), shown in a configuration of one emitting fiber optic 101 (in the center) surrounded by eight collecting bundles 102. A fiber optic bundle 100 is only one example, and the fiber optic bundle may be otherwise configured, such as containing one emitter and one or several sensor fibers, in a ratio of one emitter to one sensor up to one emitter to twelve sensors. The number of emitters could be increased and the spaces between emitters and detectors changed. The emitters and detectors might also be placed along the length of the probe as opposed to its end. The fiber optic bundle 100 may be positioned on or within a tissue sample. Re-emission from the tissue sample is collected in back-scattering configuration by the same fiber optic bundle. The end of the fiber optic bundle preferably is placeable directly onto the surface of a tissue such as the oral mucosal or heart. Alternatively, the fiber optic bundle is placeable directly into a tissue such as the brain or liver. The fiber optic arrangement does not require contact with the tissue especially when extraneous light (ambient light) is prevented from entering the fiber optic sensor.

A preferred example of an invasive fiber optic probe is one that is less than 0.2 mm, and which can be rapidly placed singularly or in an array in a muscle bed through a small gauge hypodermic needle. When such a needle is used to place a probe, after insertion the needle may then be removed and the probe secured in place such as by medical tape.

Again referring to FIG. 26(a), the light collected by the fiber optic is notch filtered by a laser notch filter system 200 (comprising at least one and preferably two laser notch filters) and then distributed to a spectrograph system 300 (preferably such as a spectrograph system comprising a Raman spectrograph system and a fluorescence spectrograph system). The spectrograph system 300 has a respective CCD detector system 400 associated with it. The CCD detector system preferably comprises a CCD detector for each spectrograph system, i.e., when using a Raman spectrograph system with a fluorescence system, the Raman spectrograph system has an associated CCD detector and the fluorescence system has an associated CCD detector. The CCD detector system 400 provides signals to a signal analyzer 500 (such as a PC type computer). It will be appreciated that respective systems 200, 300 and 400 each respectively may include one, two, three or more components, with some examples of such systems being given in FIGS. 26(*b*), 26(*c*) and 26(*d*). Preferably, laser notch filter system 200 comprises at least one laser notch filter, spectograph 300 comprises at least one spectrometer and CCD detector system 400 comprises at least one CCD detector.

In a particularly preferred embodiment of the invention, an exemplary device is provided incorporating both Raman spectroscopy and fluorescence spectroscopy. The exemplary device according to FIG. 26(*b*) is an example of such an inventive device combining Raman and fluorescence spectroscopy. With reference to FIG. 26(*b*), the light collected by the fiber optic is notch filtered 2, 2'*b* and distributed to spectrometers such a spectrograph system set for Raman 3 and a spectrograph set for broadband fluorescence 30. An example of the Raman spectroscopy system 3 may include two spectrometers containing high groove density gratings, one set to collect Raman scattering between 300 and 3700 $cm^{-1}$ from the laser line (collecting the Raman signal of water to use as an intensity standard) and one set to collect Raman scattering between 1200 and 1700 $cm^{-1}$ (heme vibrations). An example of the fluorescence spectroscopy system 30 contains a low groove density grating and is set to collect broadband fluorescence emission within the region 200 to 800 nm. The Raman spectrograph system 3 has a respective CCD detector system 4 associated with it, and the fluorescence spectroscopy system 30 has a respective CCD detector system 40 associated with it. The CCD detector systems 4, 40 provide signals to an analysis system, such as a PC type computer 5.

With an equipment set-up according to FIG. 26(*b*), levels of oxyhemoglobin, deoxyhemoglobin (and thus tissue hemoglobin saturation), and NADH accumulation, may be determined. Information necessary to determine blood pH within the tissue as well as the absolute concentration of hemoglobin within the tissue may be obtained. As for computing concentration, an example may be appreciated with reference to FIG. 27, demonstrating that the resonant Raman spectroscopy technique can detect differences in the amount of hemoglobin present. Hemoglobin levels (in absolute terms) may be determined in tissue, by examining the intensity of the signals (y-axis in FIG. 27). The more hemoglobin present in the tissue, the higher the resulting signal intensity. These intensities may be compared to known standards for the determination of hemoglobin amount.

Another example of an exemplary inventive device is one comprising an electromagnetic radiation generator (such as a laser) with a wide range of selectable wavelengths (such as deep ultraviolet, less than 270 nm to shortwave infrared all the way to 20,000 nm), filters, lenses, fiber optics, a charge coupled device (CCD), a spectrograph, and the software necessary to interpret the Raman shifts. The device can obtain resonance Raman spectra at a variety of wavelengths corresponding to the "fingerprint" or "signature" of molecules associated with tissue oxygen metabolism (such as hemoglobin (Hb), myoglobin (Mb), cytochrome oxidase (cyt a, a3), dissolved or free gases (i.e., $O_2$, $CO_2$, CO, NO, etc. in tissues, exhaled respiratory gas or intraluminal gastrointestinal gas), glucose, lactate, pyruvate, and bicarbonate. Various mediators associated with shock such as tumor necrosis factor (TNF) and other pro and anti-inflammatory cytokines, catecholamines (epinephrine, norepinephrine and dopamine), general and destructive proteins such as albumin and myeloperoxidase respectively, high energy phosphates (ATP, PCr, ADP, Pi), metabolic energy intermediates (NAD, NADH), excitatory amino acids (glutamate, aspartate), and vasocative peptides (vasopressin, angiotensin II, natriuretic peptides, etc.) can also be measured with such a technique.

Devices according to the invention may be used in a multiparametric system for non-invasive or minimally invasive monitoring of tissue perfusion and metabolism in critically ill or injured patients. Because the technique permits identification of an almost unlimited number of target compounds, ultra-early detection may be provided, as well as complete characterization and differentiation of various pathologic states. The invention provides also for determining when treatment is complete. The inventive methods and devices may be applied with regard to various shock states, and ischemia of various organ or organ systems such as the heart, brain, and gastrointestinal tract. Probes for the device may be placed within any tissue bed to monitor the state of a specific tissue. The probes and techniques also may be used to reflect the state of the organism as a whole. Probes may be constructed for intravascular placement as well as placement into other devices such as urinary catheters, gastrointestinal tubes and endoscopes, heart catheterization equipment, brain and other tissue monitoring devices.

Devices may used in the operating room to examine target molecules and the status of various organs such as the liver, GI tract, brain or heart or other tissues of interest. Implantable probes may be placed in transplanted tissues to allow for their interrogation at subsequent time points to monitor for rejection.

In another preferred embodiment, the invention provides a method of diagnosing shock, tissue ischemia, tissue inflammation, or tissue immune dysfunction, comprising: (A) for a target molecule population, taking a sample Raman spectroscopy, and/or fluorescence spectroscopy, profile for a patient; (B) comparing the sample spectroscopy profile with a pre-established Raman spectroscopy and/or fluorescence spectroscopy profile for the target molecule population under baseline conditions. A further preferred embodiment provides a spectroscopy comparative profile, comprising: a pre-established Raman spectroscopy and fluorescence spectroscopy profile for a target molecule population under baseline conditions; and a sample Raman spectroscopy and fluorescence spectroscopy profile for the target molecule population.

The profiles according to the invention may be of relative amounts, or of absolute amounts. The sample profile may be taken from a tissue or a space in a body, or taken from a tissue or a space out of the body. The respective profiles are not required to be from the same species. The comparative profiles in a preferred example include a pre-established fluorescence spectroscopy profile for NADH under baseline conditions and a sample fluorescence profile for NADH. In another preferred example, a spectroscopy comparative profile includes a pair of Raman spectroscopy profiles and a pair of fluorescence spectroscopy profiles (such as one Raman spectroscopy profile and one fluorescence spectroscopy profile taken from a patient after a medical event concerning the patient).

Preferred examples of target molecule populations are NAD/NADH; lactate/pyruvate; PCr-ATP; ATP-ADP; PCr-Pi; oxidized cytochrome oxidase to reduced cytochrome oxidase, and/or oxyhemoglobin with deoxyhemoglobin. However, it will be appreciated that further potential target molecule populations may be screened and selected as target molecule populations according to the invention.

Desired features of a marker(s) of tissue perfusion are its early change after injury; and, that its normalization would indicate that resuscitation is complete. This would help to ensure that shock is detected at its earliest possible time point and that resuscitation would not be prematurely stopped. In addition, the marker(s) would not be subject to misinterpretation from factors such as changes in minute ventilation, pain, etc.

Experimentation: Markers

Using lab bench versions with diode array detection, Raman spectroscopy was used in the UV and NIR in both reflectance and transmission mode to identify several compounds having utility as markers of hemorrhage severity and its sequelae. The first group are oxygen sensitive markers of ischemia and include hemoglobin (Hb), myoglobin (Mb) and cytochrome oxidase (Cyt $aa_3$). The second group is of exquisitely sensitive oxygen-related metabolic markers of shock including lactate, pyruvate, nicoteinamide adenine dinucleotide phosphate (NAD) and NAD reduced form (NADH). A third group includes the high-energy phosphates phosphocreatine (PCr), adenosine-5'-triphosphate (ATP) and adenosine-5'-diphosphate (ADP). The fourth group includes the vasoactive chemicals epinephrine and norepinephrine.

Figure 27:
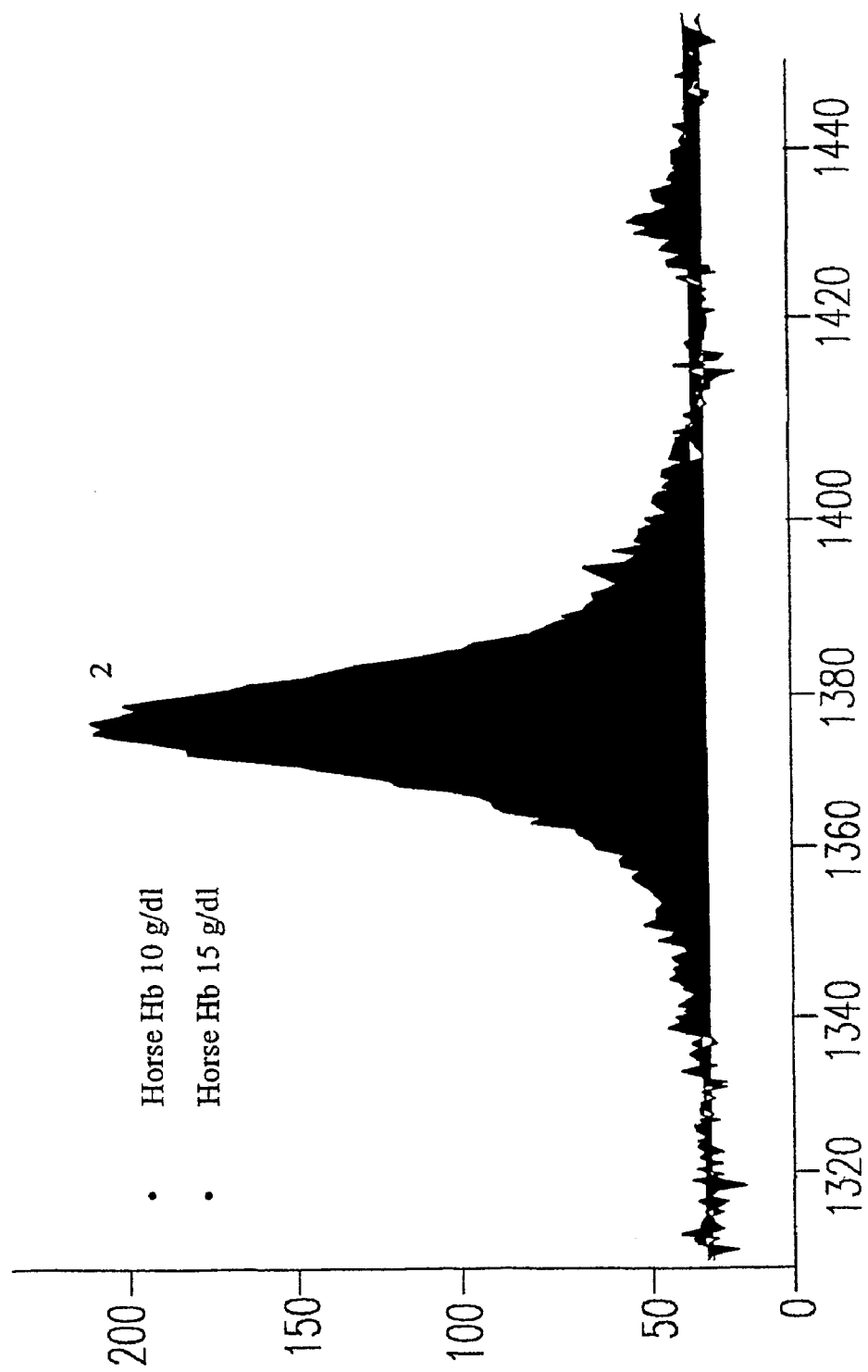
FIG. 27 depicts resonant Raman spectra for horse Hb dilutions.

Raman spectra were obtained of post-hemorrhage markers in inflammation such as lipopolysaccharide (LPS) and cytokines such as tumor necrosis factor-alpha (TNF-α). Sample spectra of lactate, pyruvate NADH, NAD, PCr, and ATP are shown in FIGS. 27(*a*), 27(*b*) and 27(*c*). Lactate and pyruvate can be easily discriminated by comparing the intensities measured at 1625 $cm^{-1}$. NAD/NADH can be discriminated by examining the peak around 1690 1625 $cm^{-1}$. PCr can be separated from other high-energy phosphates with the intensity at 1475 $cm^{-1}$ while ATP and ADP can be separated with the peaks at 1100 and 1400 $cm^{-1}$.

Of particular interest in detecting the presence and severity of hemorrhagic shock are lactate/puruvate, NADH/NAD, PCr/ATP ratios and the redox status of cytochrome oxidase in skeletal muscle. In addition, hemoglobin concentration, oxygen saturation, and potentially myoglobin oxygen saturation may be obtained. The lactate/pyruvate ratio provides information on the coupling of glycolysis to oxidative phosphorylation, the NADH/NAD ratio provides information concerning the mitochondrial energy state, and the PCr/ATP ratio provides information concerning utilization of high-energy phosphate stores. Haljamae, H., "Cellular metabolic consequences of altered perfusion," in Gutierres, G., Vincent, J., eds., "Update in Intensive Care and Emergency Medicine: Tissue oxygen utilization (Springer Verlag, 1991), pp. 71–86. These indices are considered significantly more sensitive than the redox status of cytochrome oxidase or the local level of hemoglobin concentration, oxygen saturation or pH. Even so, monitoring of current NIR absorption spectroscopy derived parameters such as the redox status of cytochrome oxidase and hemoglobin concentration and saturation may be obtained with Raman spectroscopy and can be performed with greater confidence for potential quantification. One of the major advantages of the use of Raman spectroscopy over NIR absorption spectroscopy is its potential to differentiate the signal of hemoglobin from myoglobin.

Measuring lactate alone is known to be problematic because of the contribution of increased aerobic glycolysis on lactate production secondary to elevations in systemic catecholamine levels. This may occur in the absence of continuing tissue hypoxia. Luchette, F., Roboinson, B., Friend, L., McCarter, F., Frame, S. B., James, J. H., "Adrenergic antagonist reduce lactic acidosis in response to hemorrhagic shock," J. Trauma, 46:873–880 (1999). However, knowing the lactate/pyruvate ratio along with NADH/NAD and PCr/ATP ratios will provide the operator clear insight into whether true tissue hypoxia is occurring and its severity. In addition, because there is a definite lag in metabolism of lactate, restoration of adequate perfusion will likely result in return of the above ratios before normalization of lactate, thus informing the operator that instituted therapies are working or failing. Additional sensitivity could be added by external stimulation of a few muscle fibers to examine the rate of degradation and restoration of the above metabolic intermediates. Failure to normalize these values in a timely manner indicates a state of intractable shock.

The use of Raman in the near-UV and NIR has additional advantages of allowing caretakers to detect the progression of hermorrhagic shock to more complex forms of shock such as sepsis. Spectra have been obtained for inflammatory markers such as myeloperoxidase and cytokines such as TNF-α. In addition, spectra have been obtained on lipopolysaccharide, and d-lactate, which are markers indicative of intestinal barrier breakdown. Spectra on the catecholamines epinephrine and norepinephrine have been obtained. These vasoactive substances are now being recognized as sensitive markers of the level of hypoperfusion and stress caused in various shock states. These observations may be extended to vasocative peptides such as vasopressin and angiotensin, which have been measured in rat pheochromocytoma cells by Schulze et al. Schulze, H. G., Greek, L. S., Barbosa, C. J., Blades, M. W., Gorzalka, B. B., Turner, R. F. B., "Measurement of some small-molecule and peptide neurotransmitters in-vitro using a fiber-optic probe with pulsed ultraviolet resonance ultraviolet resonance Raman spectroscopy," J. Neurosci. Meth., 92:15–24 (1999).

Thus, markers mentioned herein have remarkable utility when examined in a manner of ratios. Also, absolute quantification can be obtained using embedded standards in probes placed in parallel with other emitting and sensing probes, from which can be determined an exact path length of light. The markers mentioned in this experiment were found to be detected by UV and NIR Raman spectroscopy in both the reflectance and transmission mode gives flexibility of design of methods and products according to the invention.

In Vivo Spectroscopic Experimentation

Techniques according to the invention have been successfully applied to several tissue sites in animals, demonstrating feasibility. Techniques according to the invention require no probe contact (although probe contact with tissue can take place if desired) with tissue and acquisition times are on the order of seconds.

Figure 5:
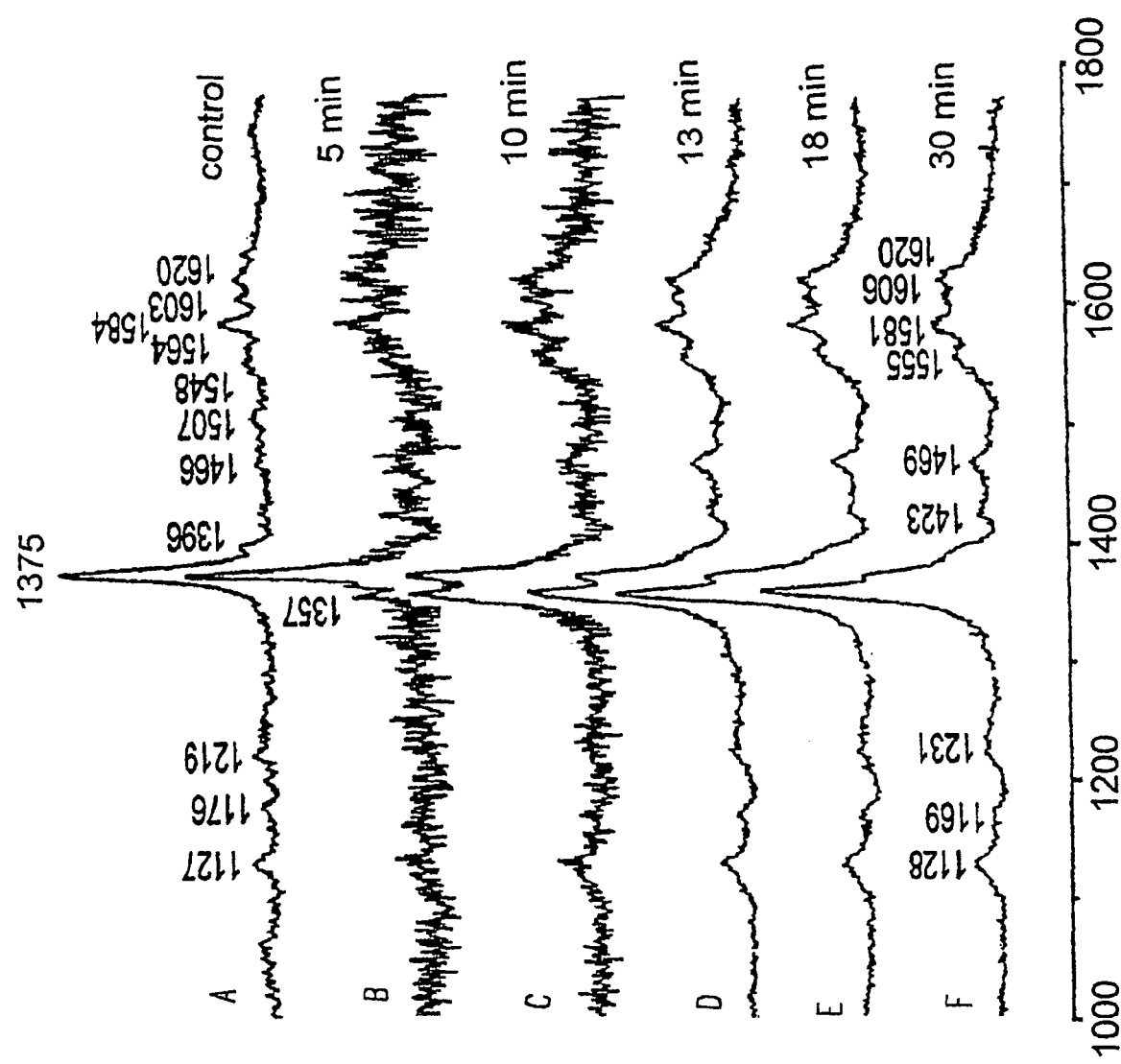
FIG. 5 shows near-UV resonance Raman spectra of isolated ischemic rat skeletal muscle over time.

FIG. 5 represents near UV resonance Raman signals taken from skeletal muscle subjected to isolated tourniquet ischemia. Signals were obtained in one minute (i.e., scans were acquired in one minute segments). The oxyhemoglobin signal (1375) decreases simultaneously to the increase in the deoxy hemoglobin signal (1357).

FIGS. 6–11 represent near UV-resonance Raman spectroscopy data of oxy and deoxy hemoglobin (with only gross signal processing) from the exposed quadriceps muscle from a rat during hemorrhage. Using area under the curve and peak height comparison analysis, tissue saturations are demonstrated to decrease during hemorrhage. Of importance is that significant tissue desaturation occurs despite the maintenance of normal vital signs. These values for oxyhemoglobin are very similar to those reported with NIR absorption spectroscopy.

Figure 6:
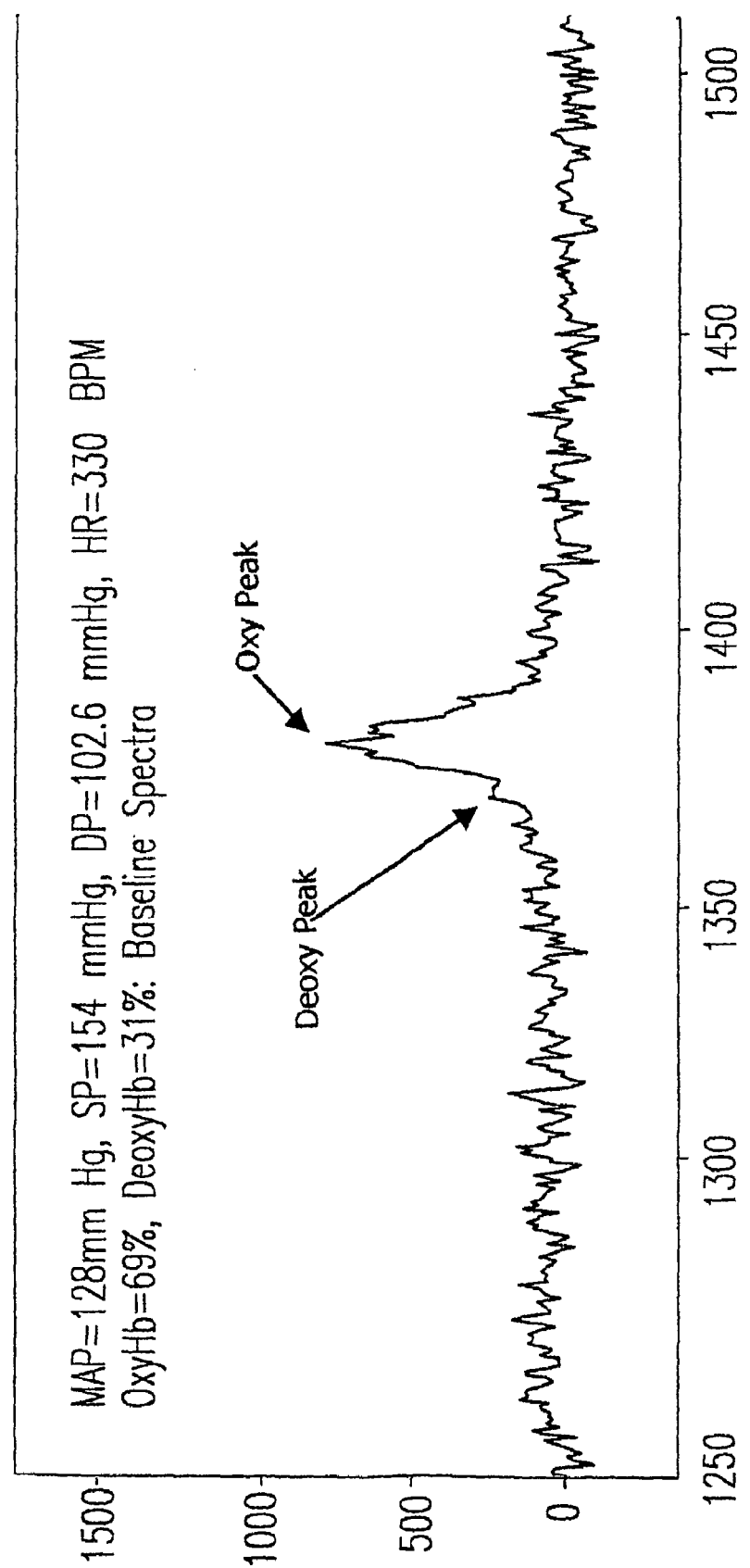
FIG. 6 is a baseline Resonance Raman spectrum for rat muscle, with the signal obtained in one second.
Figure 7:
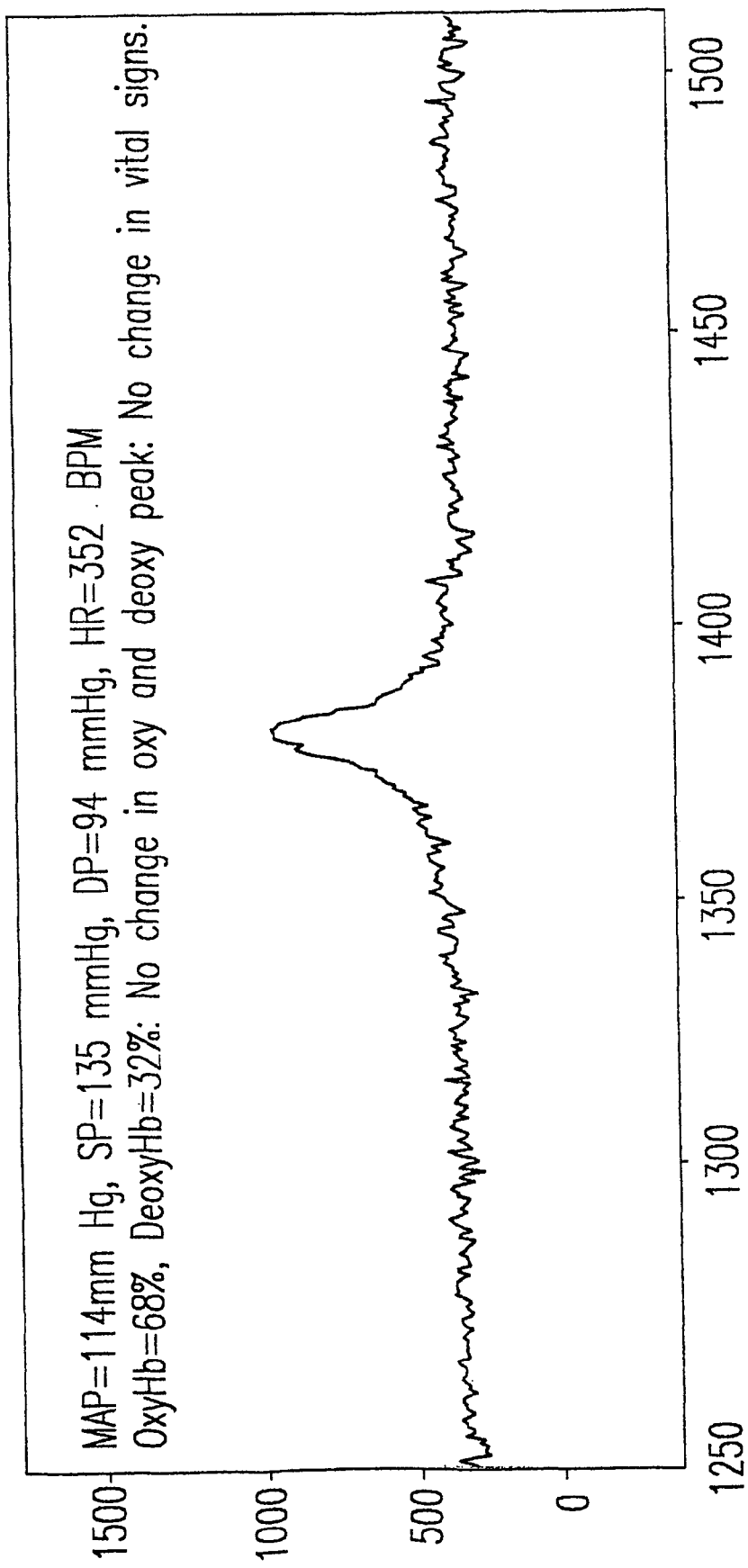
FIGS. 7, 8, 9 and 10 each is a Resonance Raman spectrum for the same muscle as FIG. 6, with respective bleeding of 1 ml, 2 ml, 5 ml and 7.5 ml.
Figure 8:
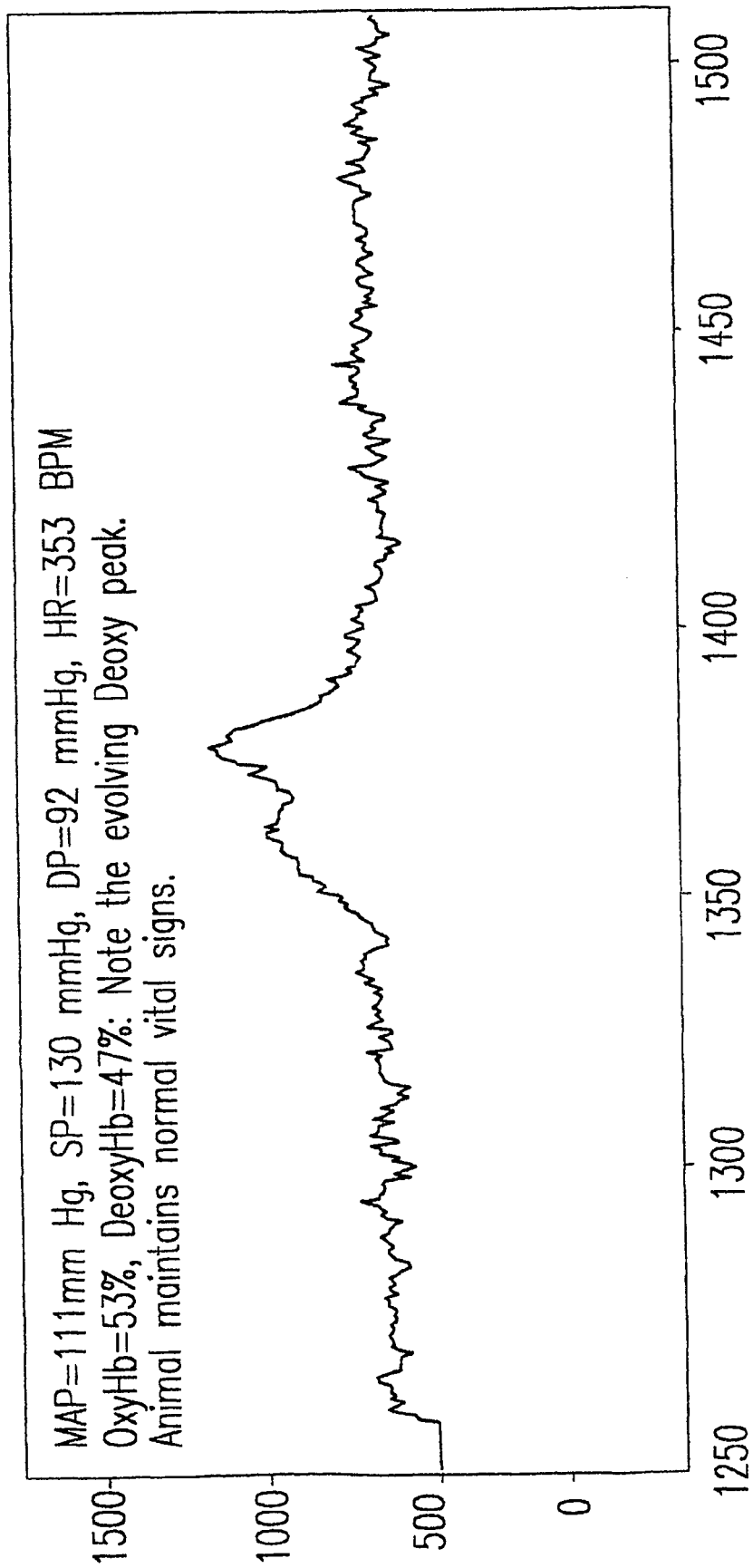
Figure 9:
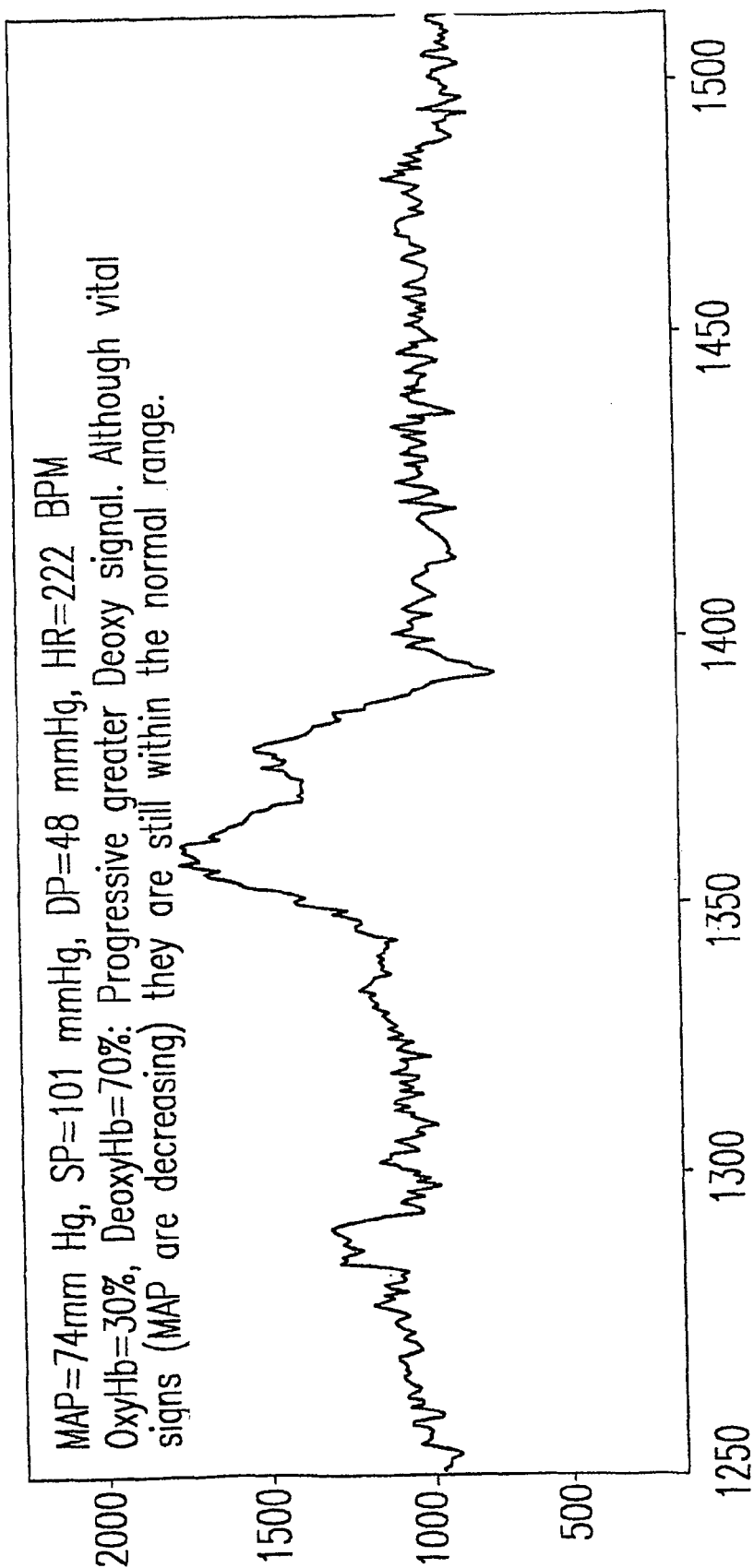
Figure 10:
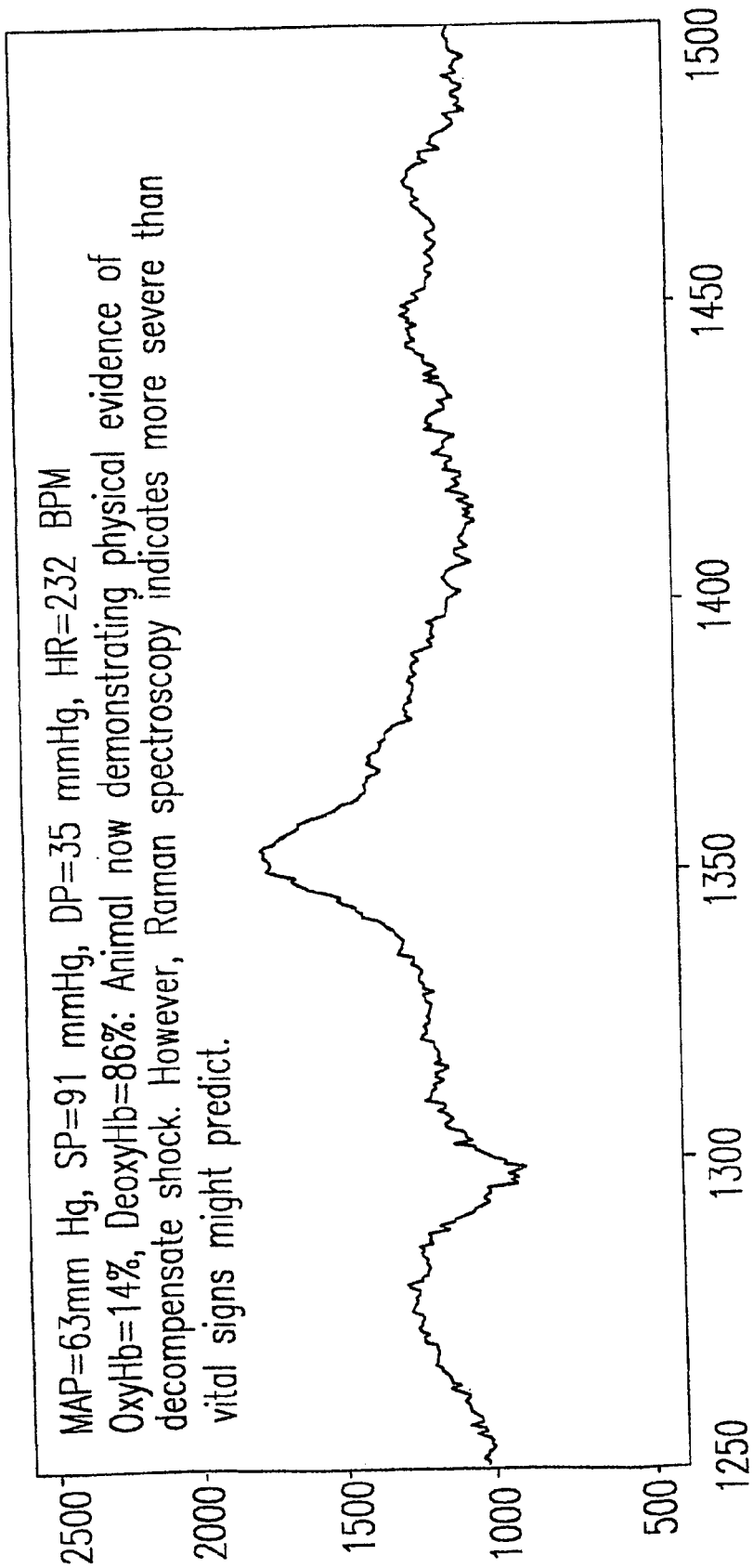
Figure 11:
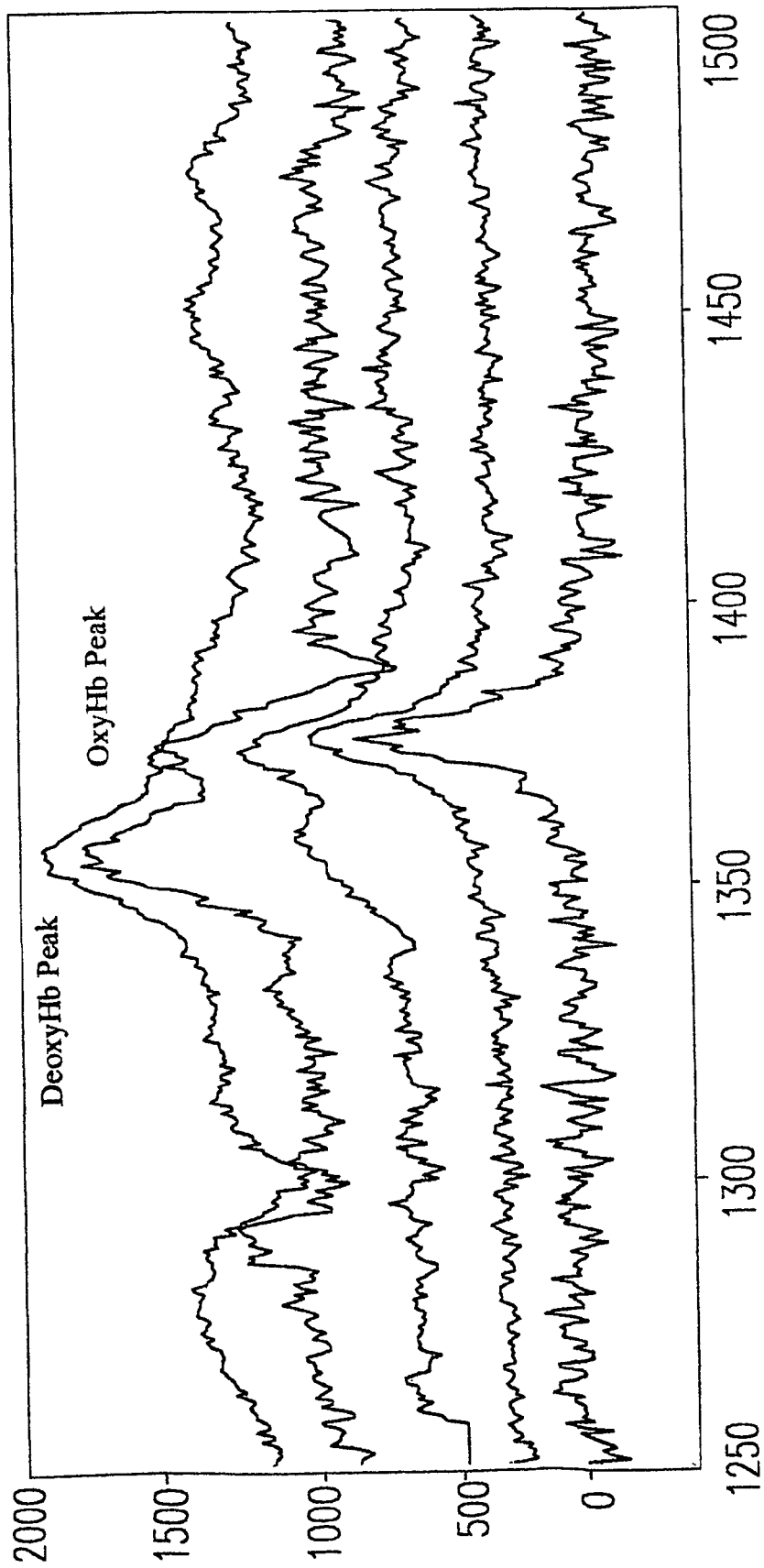
FIG. 11 is an overlay of the Raman spectra of FIGS. 6, 7, 8, 9 and 10.

FIG. 7 is for 1 ml bleeding of the same muscle as FIG. 6, which is the baseline spectrum. At 1 ml bleeding, no change in the oxy or deoxy peak was observed, and there was no change in vital signs. FIG. 8 is for 2 ml bleeding of the same muscle as FIGS. 6 and 7. At 2 ml bleeding, an evolving deoxy peak is to be noted, while the animal maintained normal vital signs. At 5 ml bleeding (FIG. 9) for the same muscle as FIGS. 6–8, a progressively greater deoxy signal is observed, and, although vital signs (MAP decreasing) are still within the normal range. Where 7.5 ml of bleeding (FIG. 10) has occurred for the same muscle as FIGS. 6–9, the animal demonstrated physical evidence of decompensate shock; however, Raman spectroscopy indicates greater severity than the vital signs might predict. Results from FIGS. 6–10 are summarized in Table 1 below.

TABLE 1

|  | OxyHb | DeoxyHb |
| --- | --- | --- |
| Baseline (FIG. 6) | 69% | 31% |
| 1 ml bleed (FIG. 7) | 68% | 32% |
| 2 ml bleed (FIG. 8) | 53% | 47% |
| 5 ml bleed (FIG. 9) | 30% | 70% |
| 7.5 ml bleed (FIG. 10) | 14% | 86% |

Figure 12:
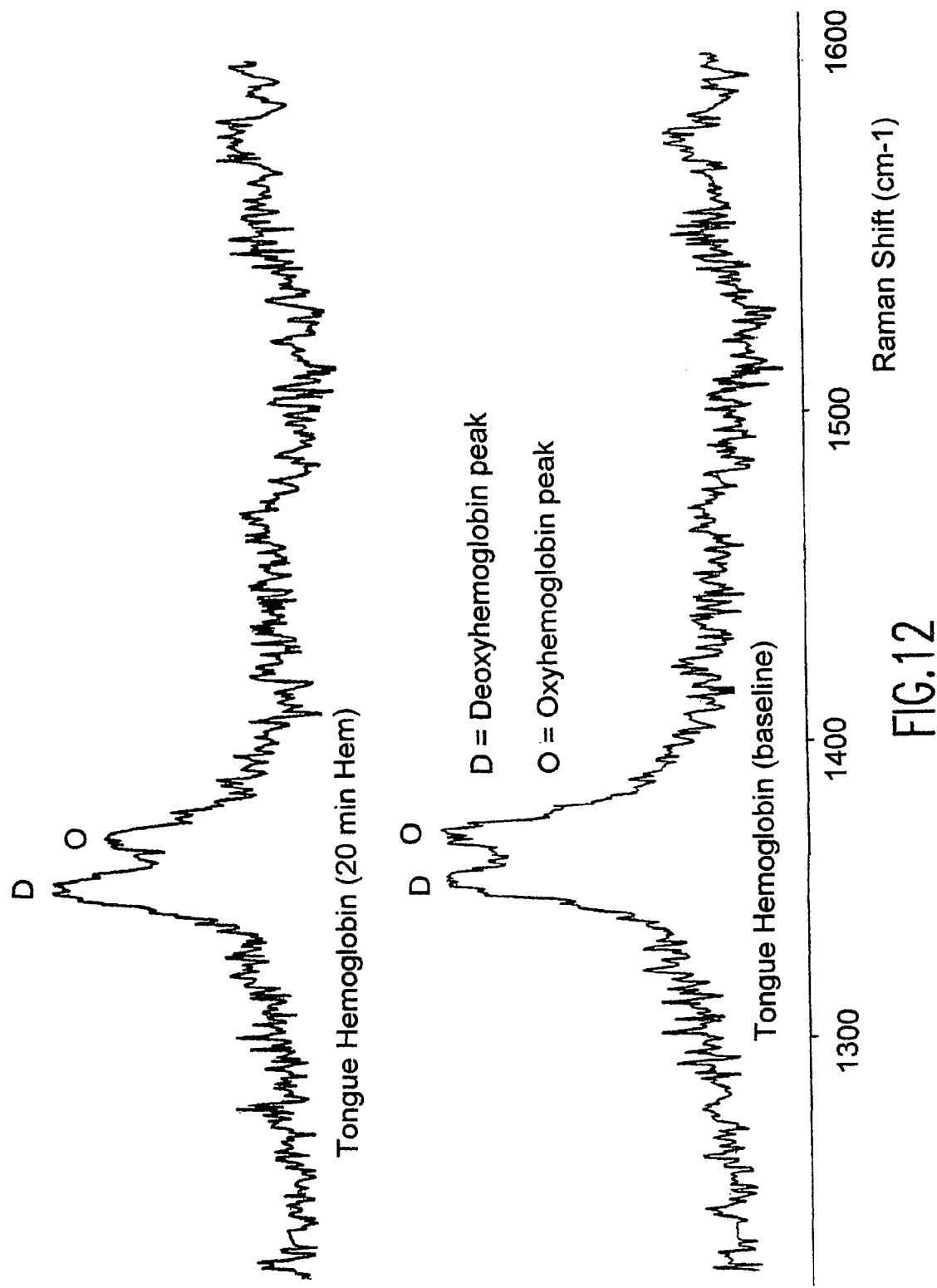
FIG. 12 are resonance Raman spectra of a rat tongue.

A similar experiment to that of FIGS. 6–11 was performed using the tongue as the target organ, as seen with reference to FIG. 12, which shows resonance Raman spectra demonstrating saturation changes during 3 cc hemorrhage. The signal was obtained in 5 seconds. Again, changes in tissue saturation occurred prior to changes in vital signs, demonstrating that the use of Raman spectroscopy according to the invention can be totally noninvasive.

Figure 13:
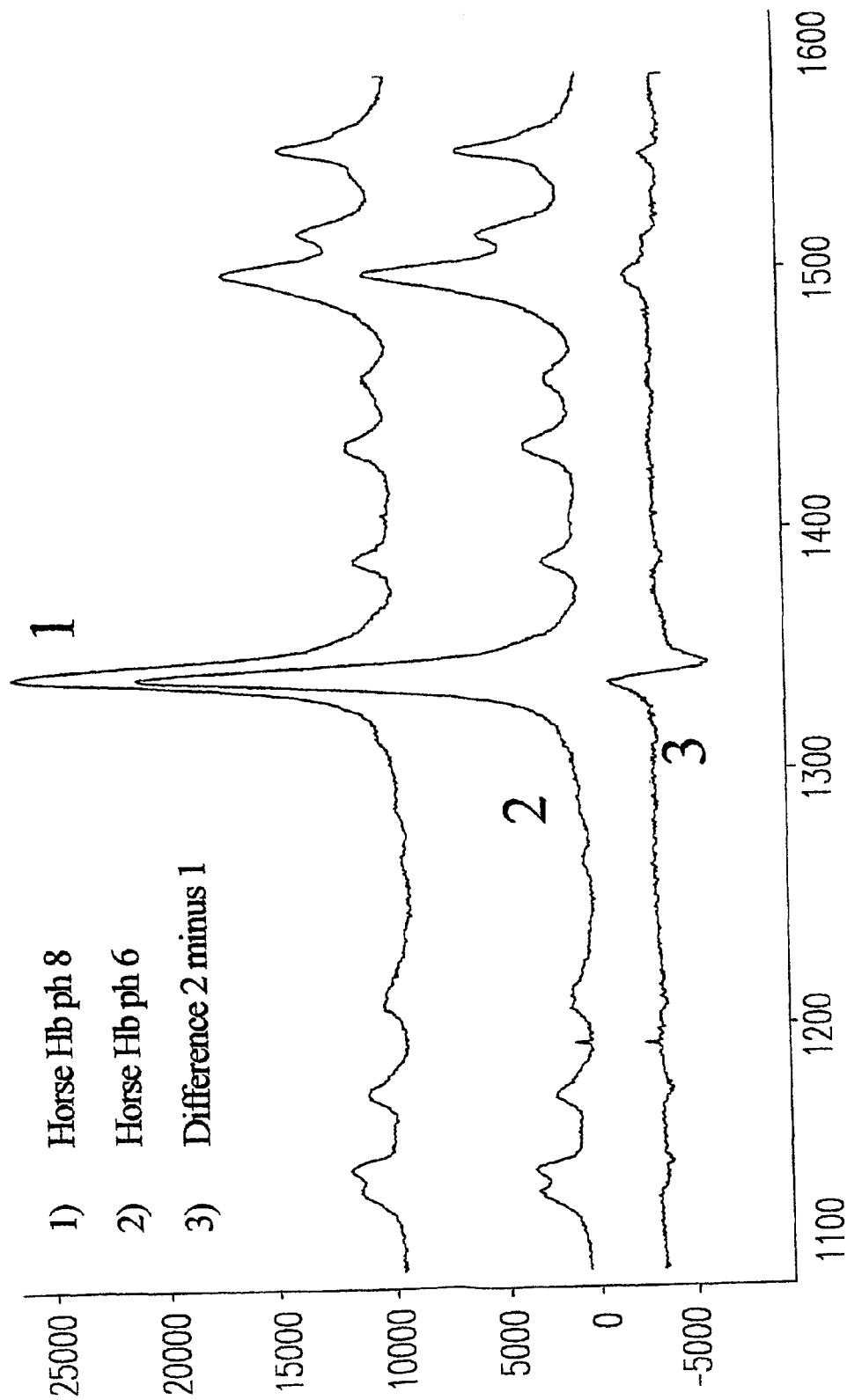
FIG. 13 are near UV resonance Raman spectra of hemoglobin.

FIG. 13 demonstrates that near-UV resonance Raman spectroscopy of hemoglobin may be used to monitor tissue pH in a manner similar to that of NIRS. The spectra of FIG. 13 are from pure oxyhemoglobin samples at different pH levels. Subtraction of the two scans provides clear evidence for a difference indicating that pH alone was responsible for the effect. FIG. 13 is for Horse Hb. Near UV resonance Raman spectra of hemoglobin are shown at pH of 8 (scan 1) and 6 (scan 2) with a subsequent subtraction scan (scan 3) demonstrating the likelihood of pH sensitive changes in the spectra.

Another important finding according to the present invention is that at this same near-UV wavelength, NADH demonstrates significant fluorescence. The present inventors have observed significant fluorescence from tissue excited in the near-UV range (406.7 nm) using a portable spectrometer. Exciting tissue in the near-UV range (406.7 nm) according to the invention provides better resolution than traditional filtering in which unique excitation light sources and detection filters are used for the conventional set-up relying on NADH fluorescing (emiting light at 460 nm) when excited at a wavelength of 360 nm (near-UV).

Based on the importance of NADH in cellular oxygen utilization (as set forth above), from this aspect of the invention may be determined the point of tissue dysoxia or critical $DO_2$ (ischemia) prior to being able to note increases in systemic lactate. Although NADH also exists in the cytoplasm, it does so in insignificant amounts compared to those produced within the mitochondria during states of dysoxia. In conjunction with the tissue saturation experiments above, NADH fluorescence from quadriceps (FIGS. 14–19), tongue (FIG. 20) and additionally liver (FIG. 21) was obtained during graded hemorrhage.

Figure 14:
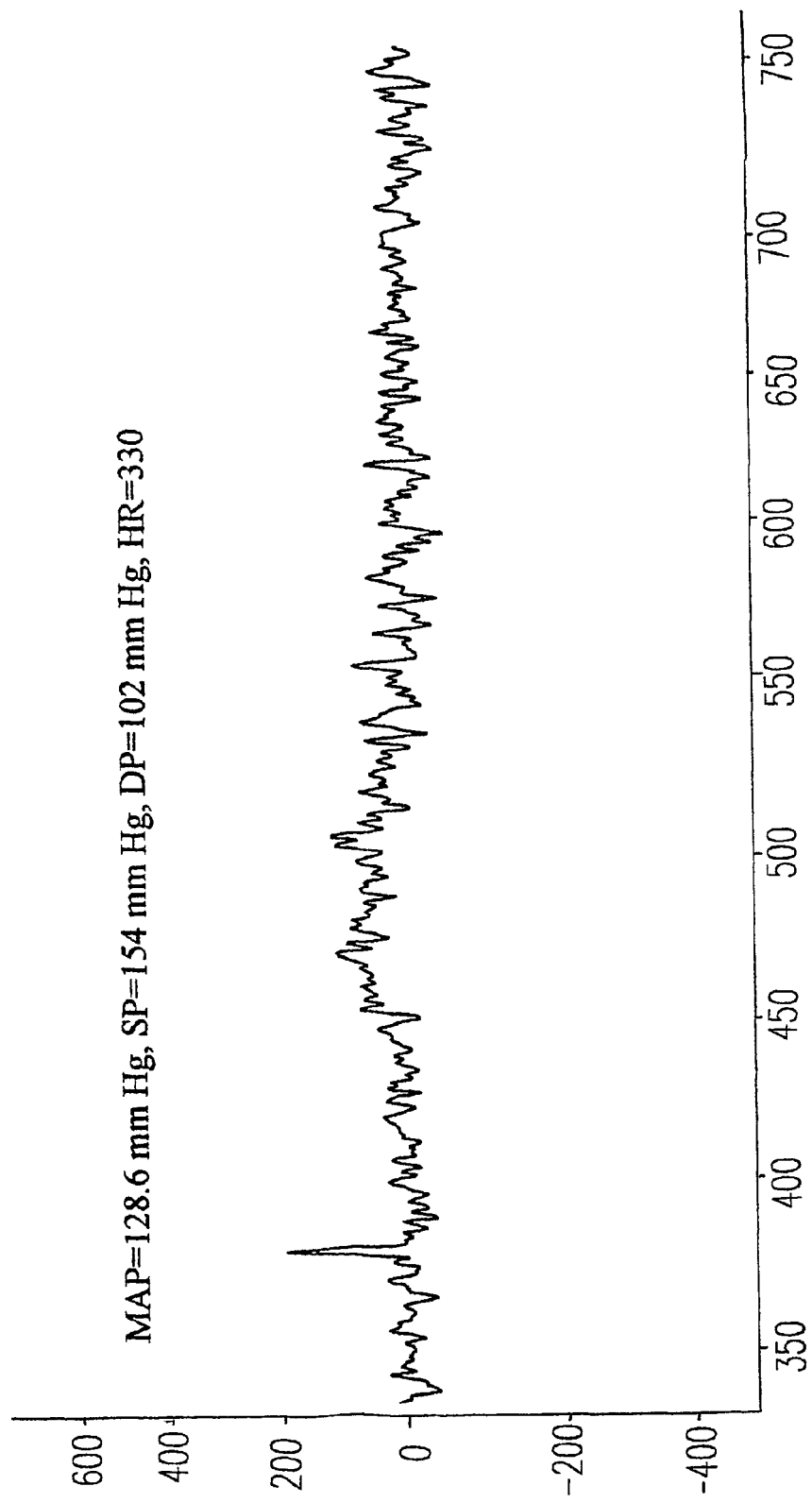
FIG. 14 is a spectra of baseline NADH fluorescence of the same quadricep muscle from the same animal in which NADH fluoresces after being excited with light at 406.5 nm which is the same wavelength used to produce the previous resonance Raman spectroscopy of FIGS. 5–10.
Figure 15:
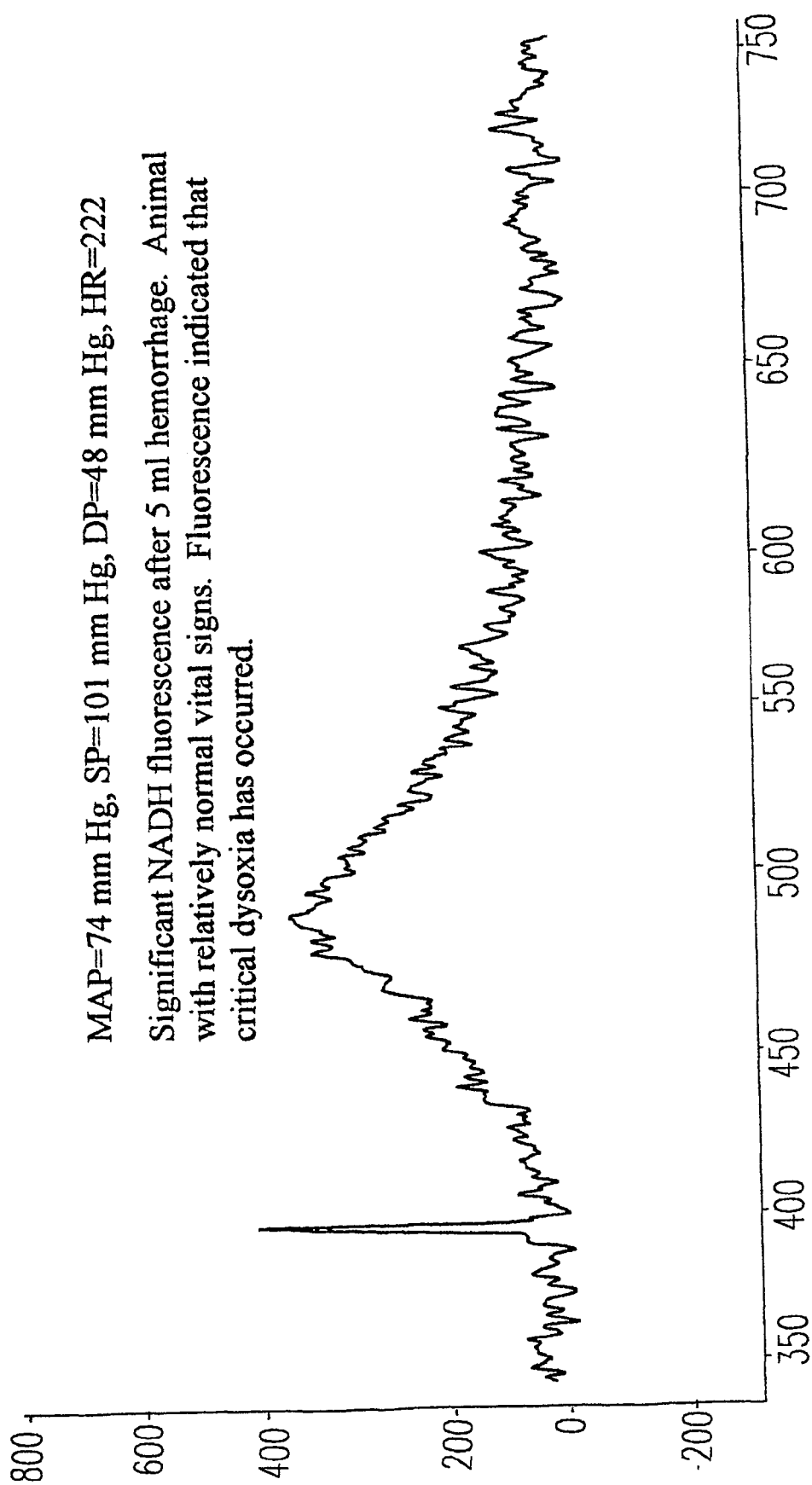
FIGS. 15, 16, 17 and 18 each is a spectra of NADH fluorescence for the same muscle as FIG. 14, with respective bleeding of 5 ml, 7.5 mls, 9 mls and 12 mls.
Figure 16:
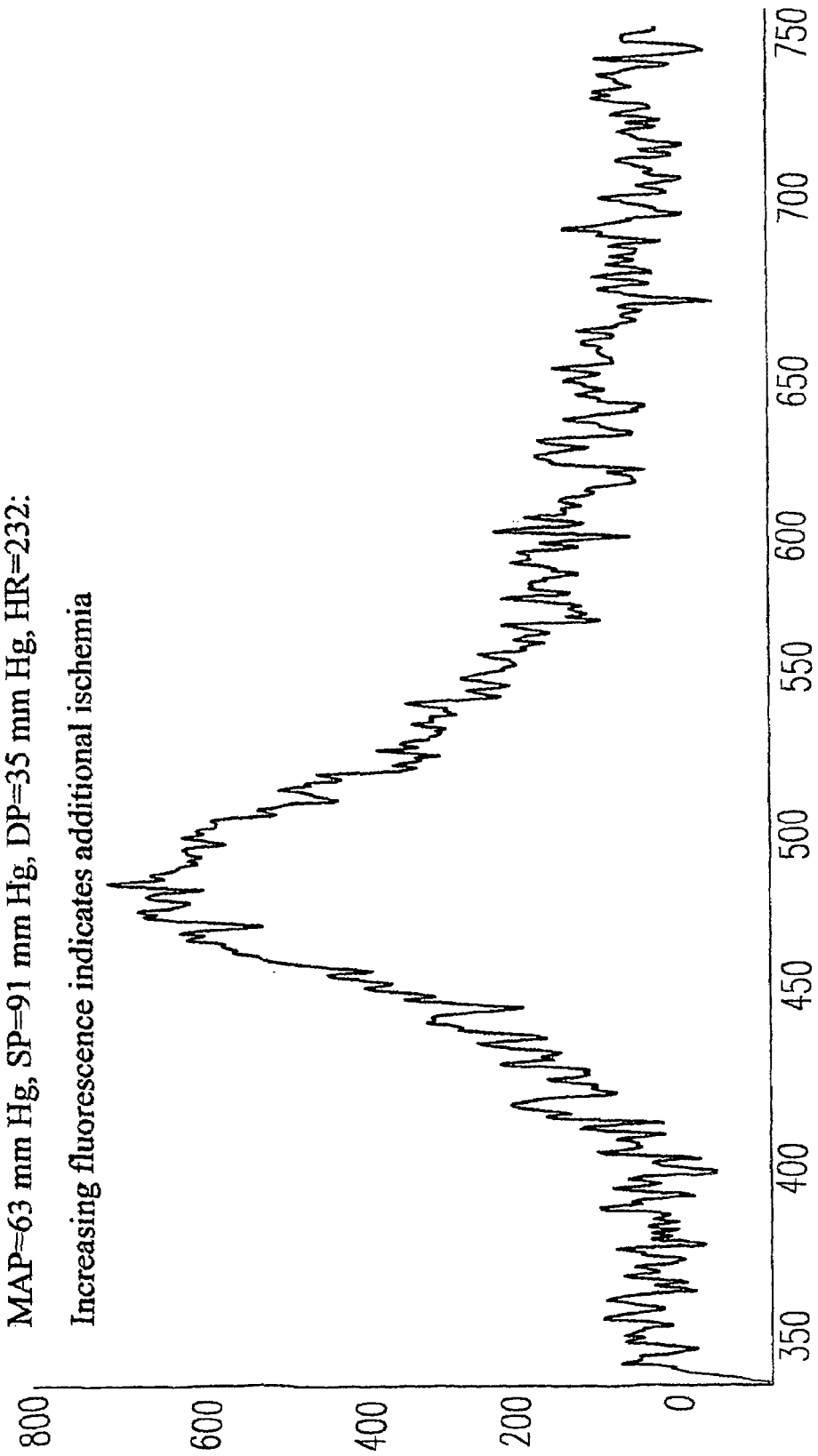
Figure 17:
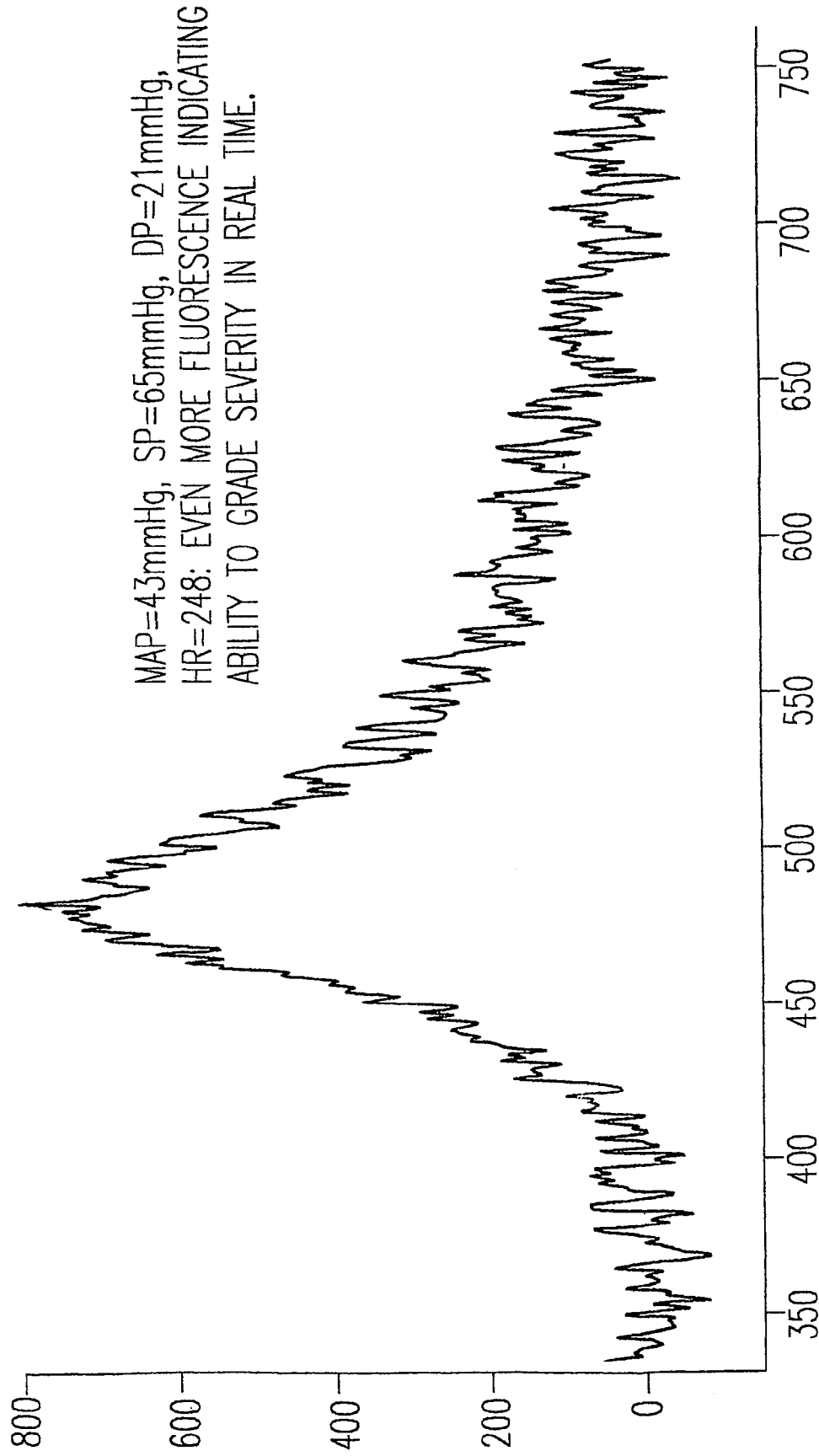
Figure 18:
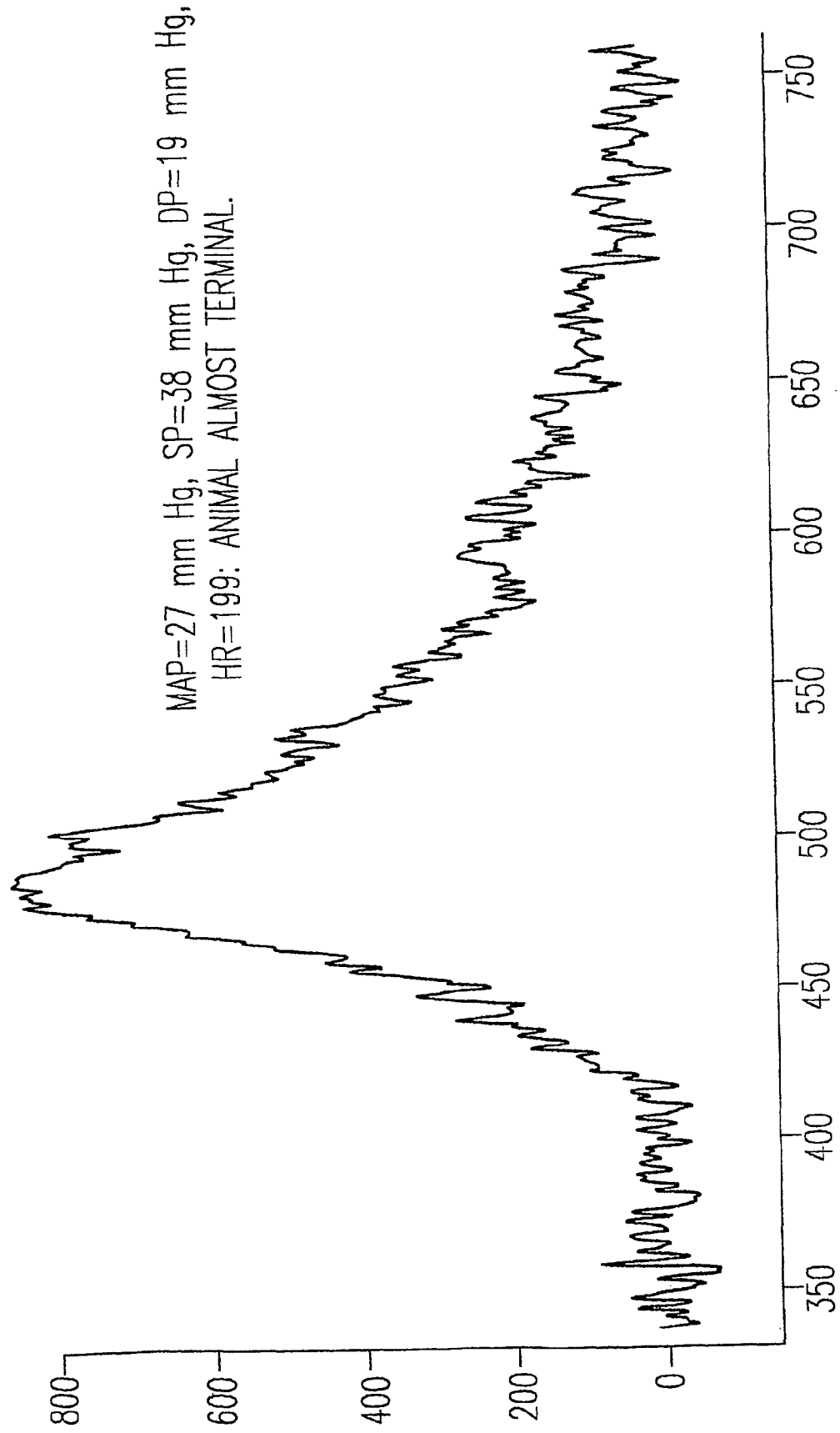
Figure 19:
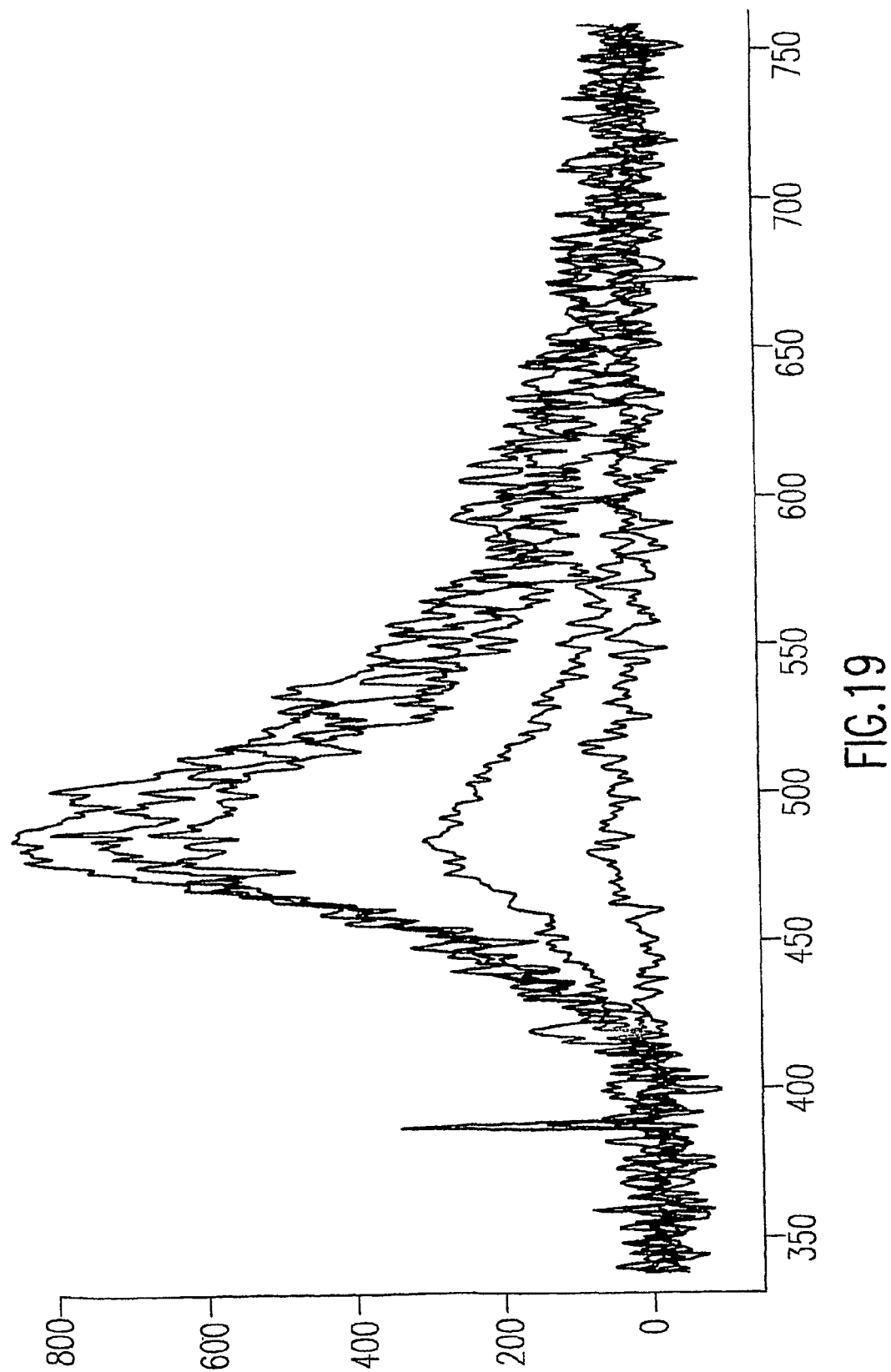
FIG. 19 is an overlay of NADH fluorescence spectra (FIGS. 14–18) from the quadriceps muscle.
Figure 20:
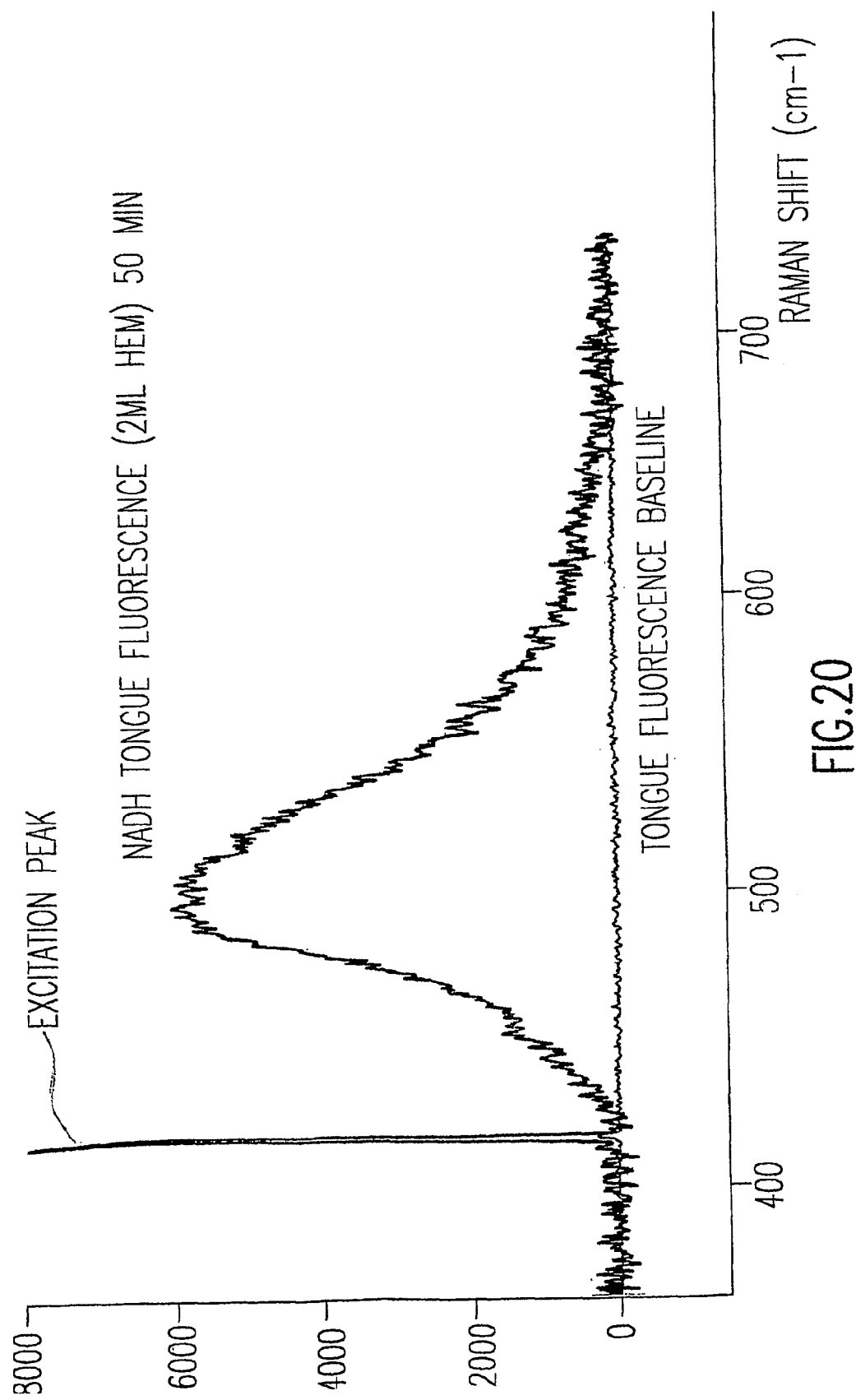
FIG. 20 is an overlay of NADH fluorescence spectra of a rat tongue, for baseline and after 2 cc hemorrhage for 50 minutes.
Figure 21:
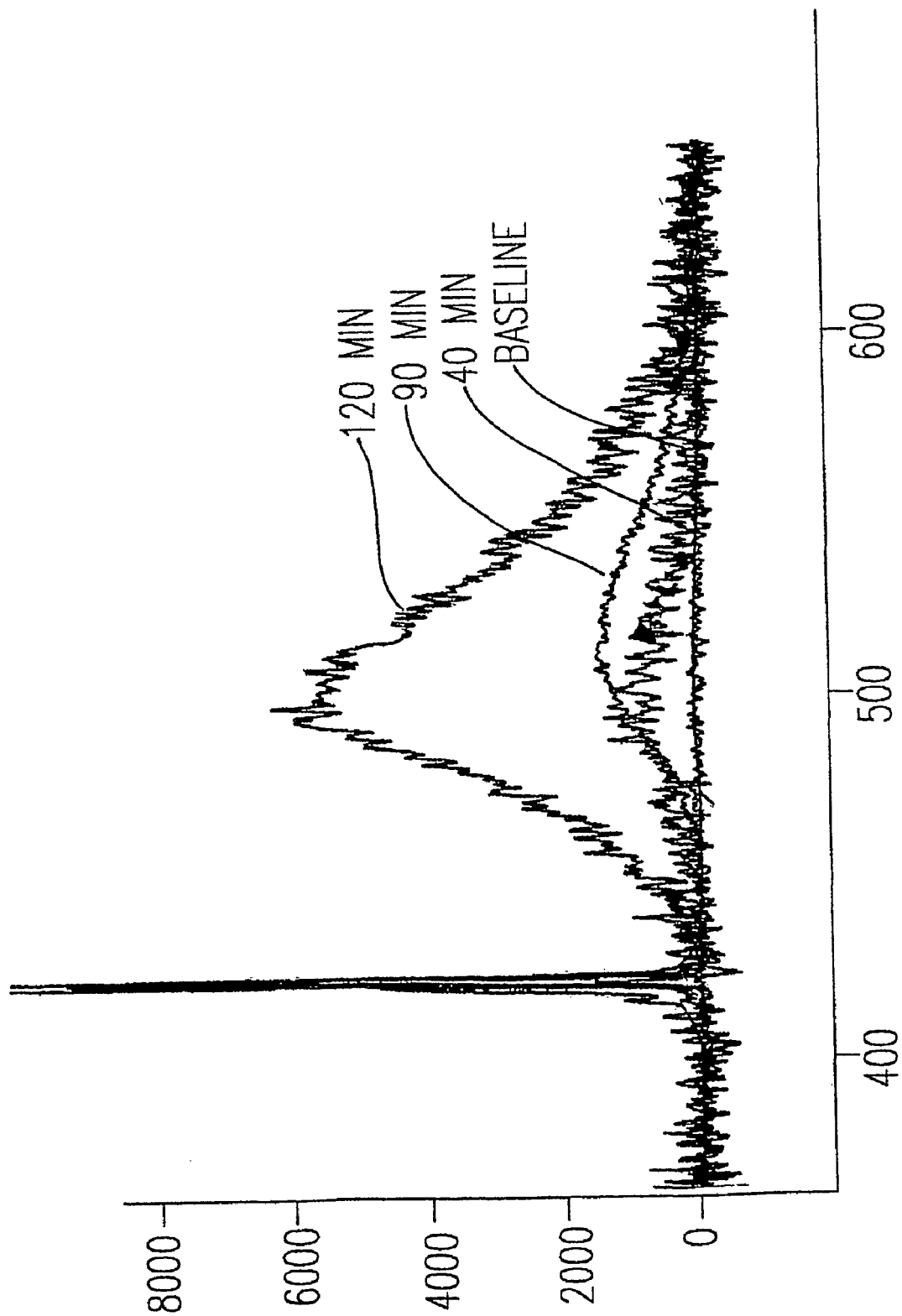
FIG. 21 is an overlay of NADH fluorescence spectra of a rat liver during graded hemorrhage over time (baseline, 40 min, 90 min and 120 min).
Figure 22A:
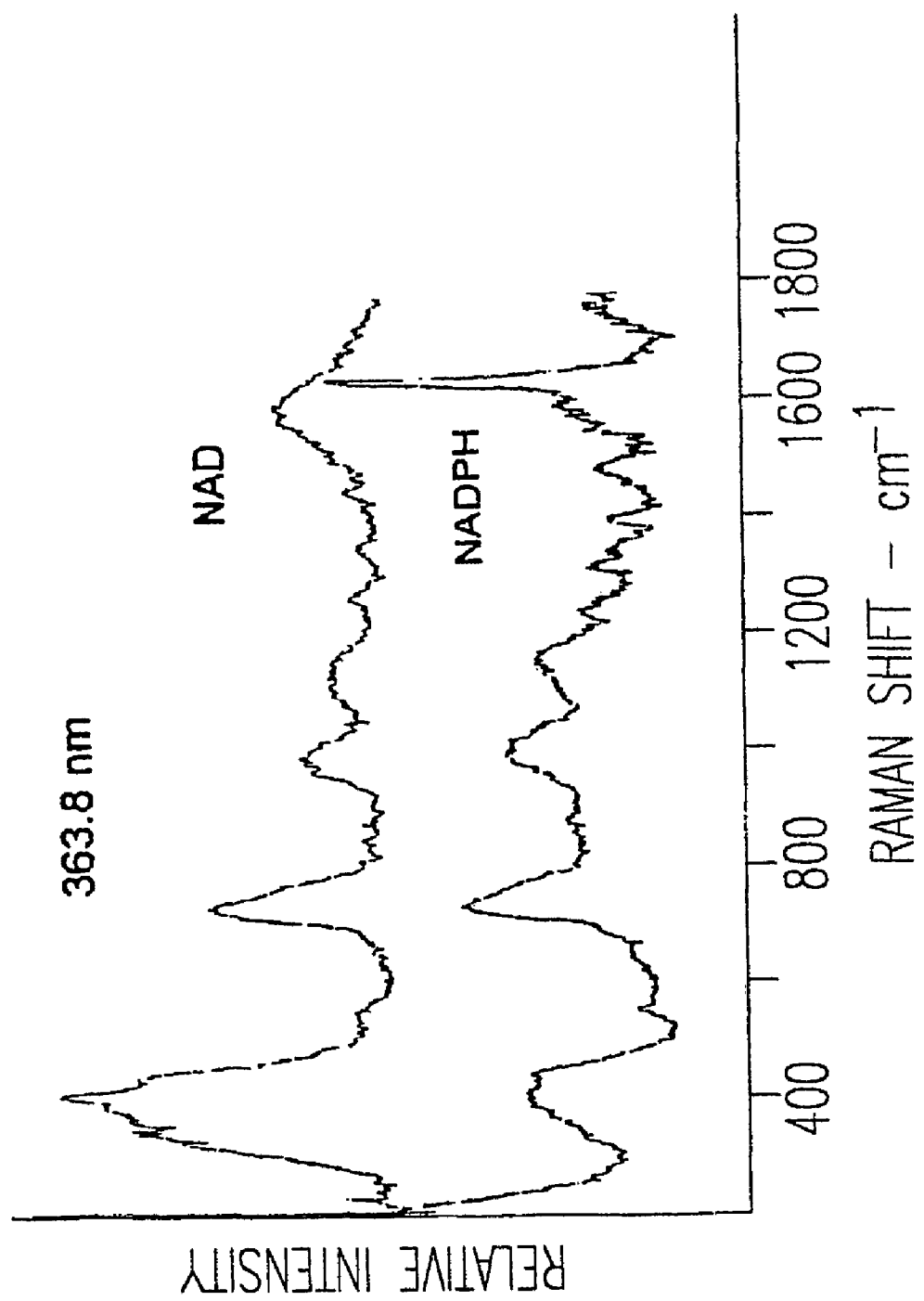
FIG. 22($a$) are preliminary Raman spectra of β-nicotinamide adenine dinucleotide in the oxidized (NAD) and reduced (NADPH or NADH) forms.
Figure 22B:
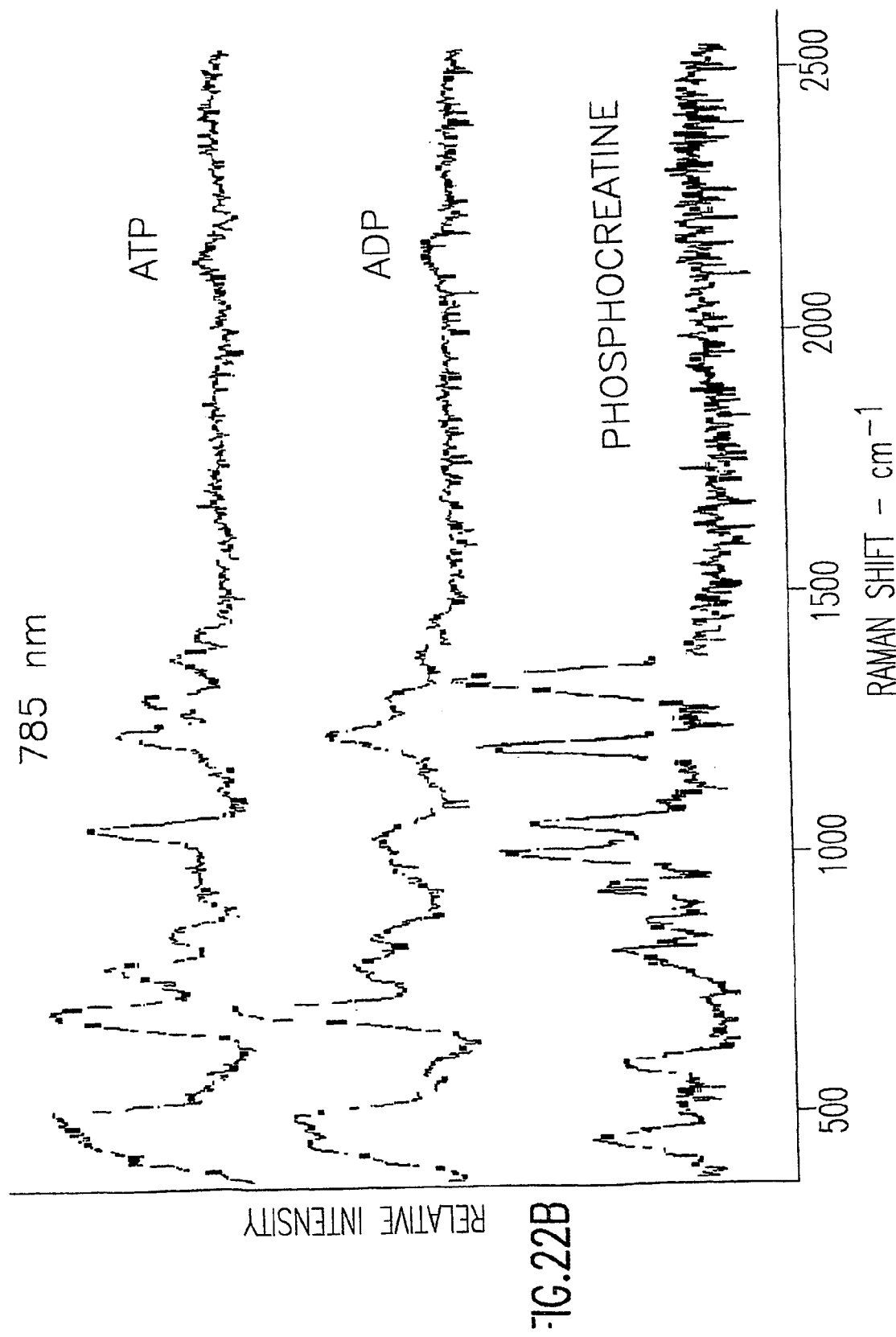
Figure 22C:
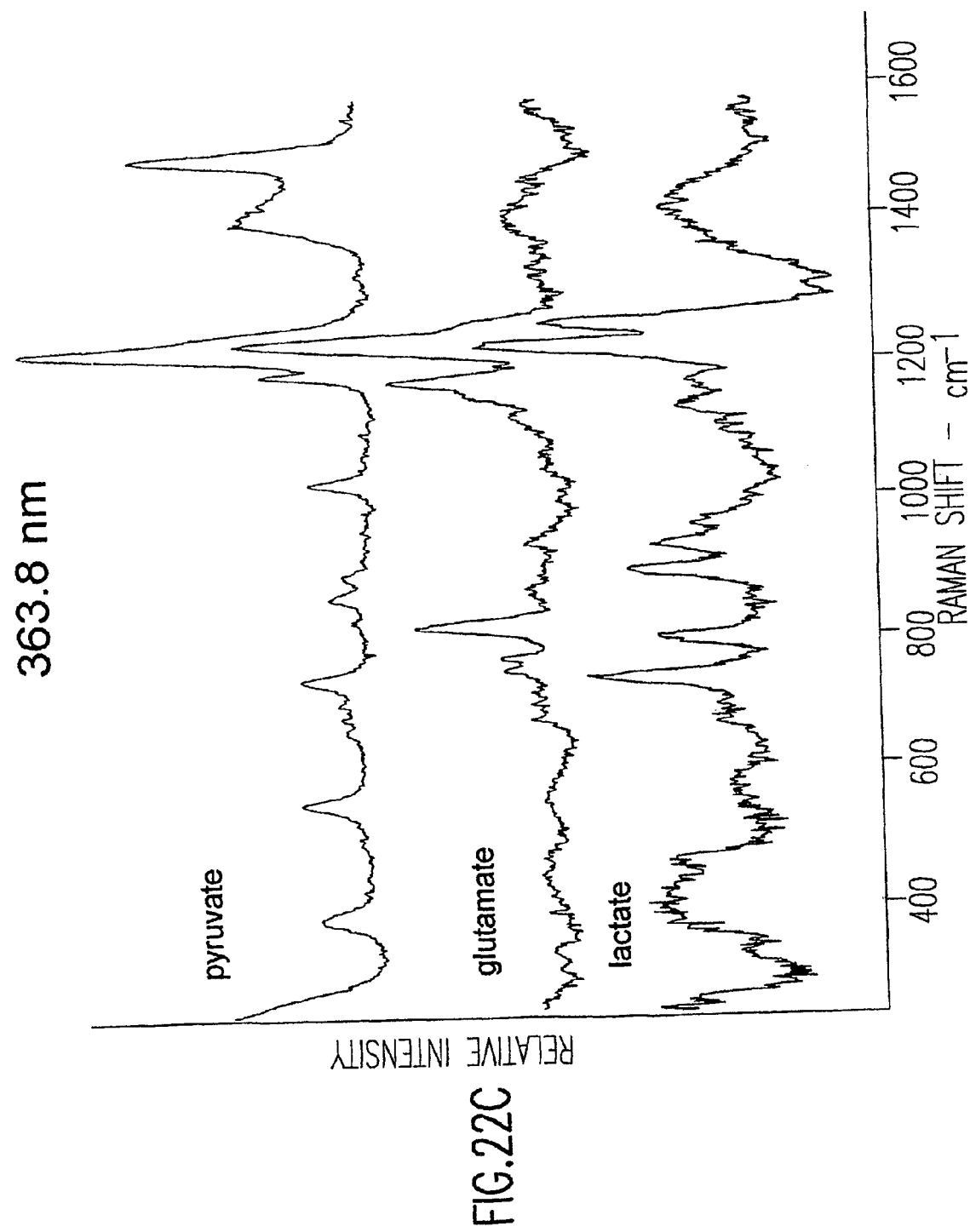
Figure 22D:
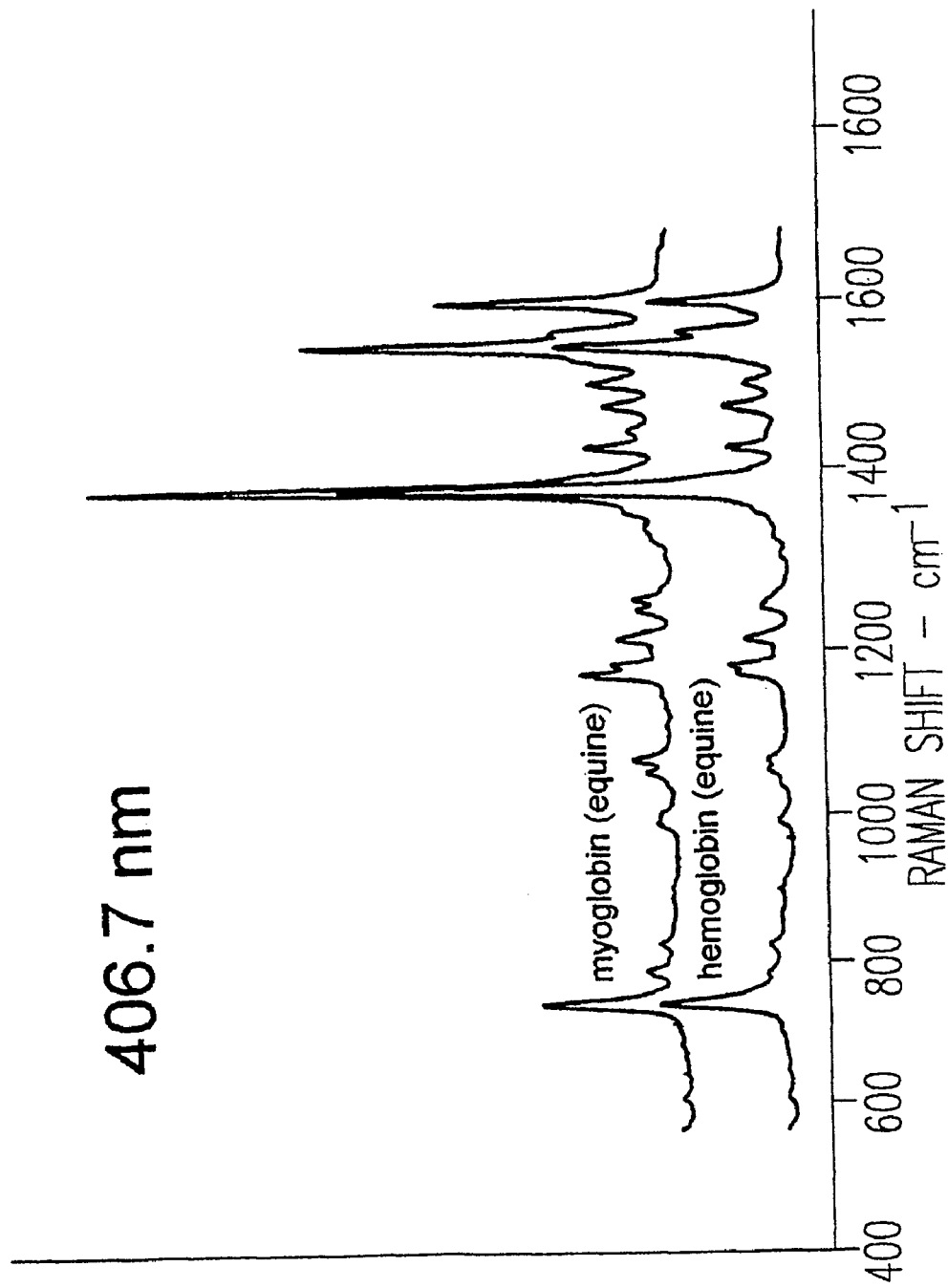
Figure 22E:
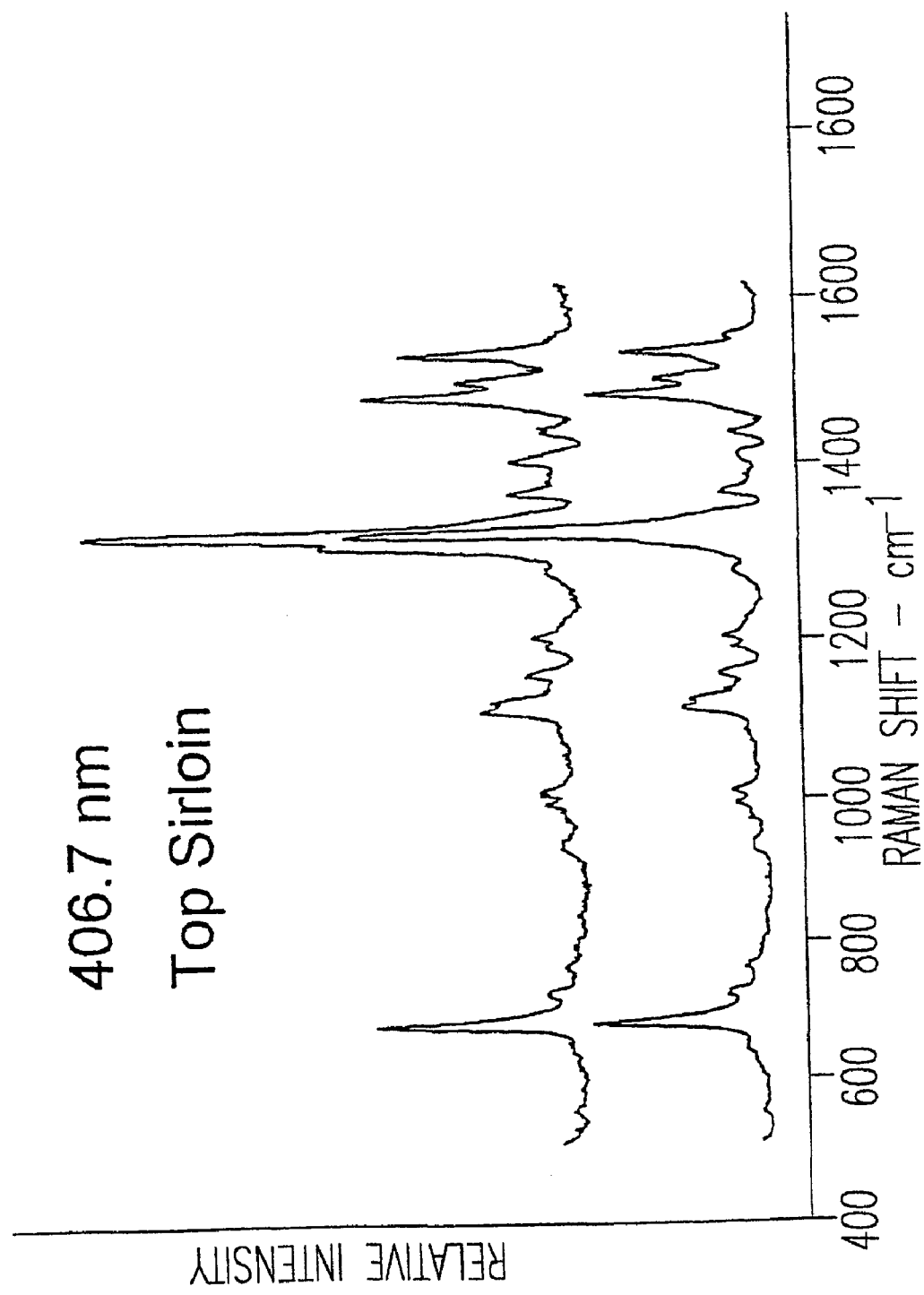

FIG. 14 is a baseline, and FIG. 15 reports spectra after 5 mls bleeding for the same quadriceps muscle. Significant NADH fluorescence is observed after 5 ml hemorrhage. Although the animal has relatively normal vital signs, fluorescence indicated that critical dysoxia has occurred. (FIG. 15.) At 7.5 mls of bleeding (FIG. 16) for the same muscle, increasing fluorescence indicates additional ischemia. At 9 mls of bleeding (FIG. 17), even more fluorescence is observed, indicating the ability to grade severity in real time. At 12 mls of bleeding (FIG. 18), the animal is almost terminal.

In the experiment in which blood pressure was monitored, significant fluorescence occurred prior to and after changes in vital signs. With equipment according to the present invention, tissue oxygen saturation and NADH fluorescence may be simultaneously obtained. Again, the depth of tissue interrogated is the same as that for tissue oxygen saturation. Thus may be determined the point at which critical oxygen delivery (dysoxia) occurs. Significant warning prior to this time will occur as reflected in reductions in tissue oxygen saturation.

Continued NADH fluorescence after restoration of oxygen delivery indicates ongoing dysoxia despite the potential for normalization of tissue oxygen saturation. The normal heart shows little or no NADH surface fluorescence. The beginning of ischemia and maximum ischemia may e observed. Continued patch fluorescence may be observed after reperfusion. Thus, NADH fluorescence data has value in monitoring tissue even after perfusion has been restored.

Because of the kinetics of lactate production and transport, it is very likely dysoxia detected by NADH accumulation and fluorescence will occur significantly earlier than with detection of regional or systemic lactate or even $CO_2$. In short, the combined use of near-UV resonance Raman spectroscopy and near-UV NADH fluorescence serve as an exquisitely sensitive early warning system for pending defects in tissue perfusion and in ensuring the completeness of resuscitation.

Other heme proteins, which have importance in ischemia-reperfusion diseases can be detected using resonance Raman spectroscopy at the same near-UV wavelength (406.7 nm). These include myeloperoxidase, which is an injurious enzyme produced and released by neutrophils, and xanthine oxidase, which is converted from xanthine dehydrogenase after reperfusion of ischemia and is responsible for the production of free radicals. Hayward, R., Lefer, A. M., "Time course of endothelial-neutrophil interaction in splanchnic artery ischemia-reperfusion," Am J Physiol 275 (6 Pt 2): H2080–6 (1998); Tan, S., Yokoyama, Y., Dickens, E., Cash, T. G., Freeman, B. A., Parks, D. A., "Xanthine oxidase activity in the circulation of rats following hemorrhagic shock," Free Radic Biol Med, 15(4):407–14 (1993).

Figure 23:
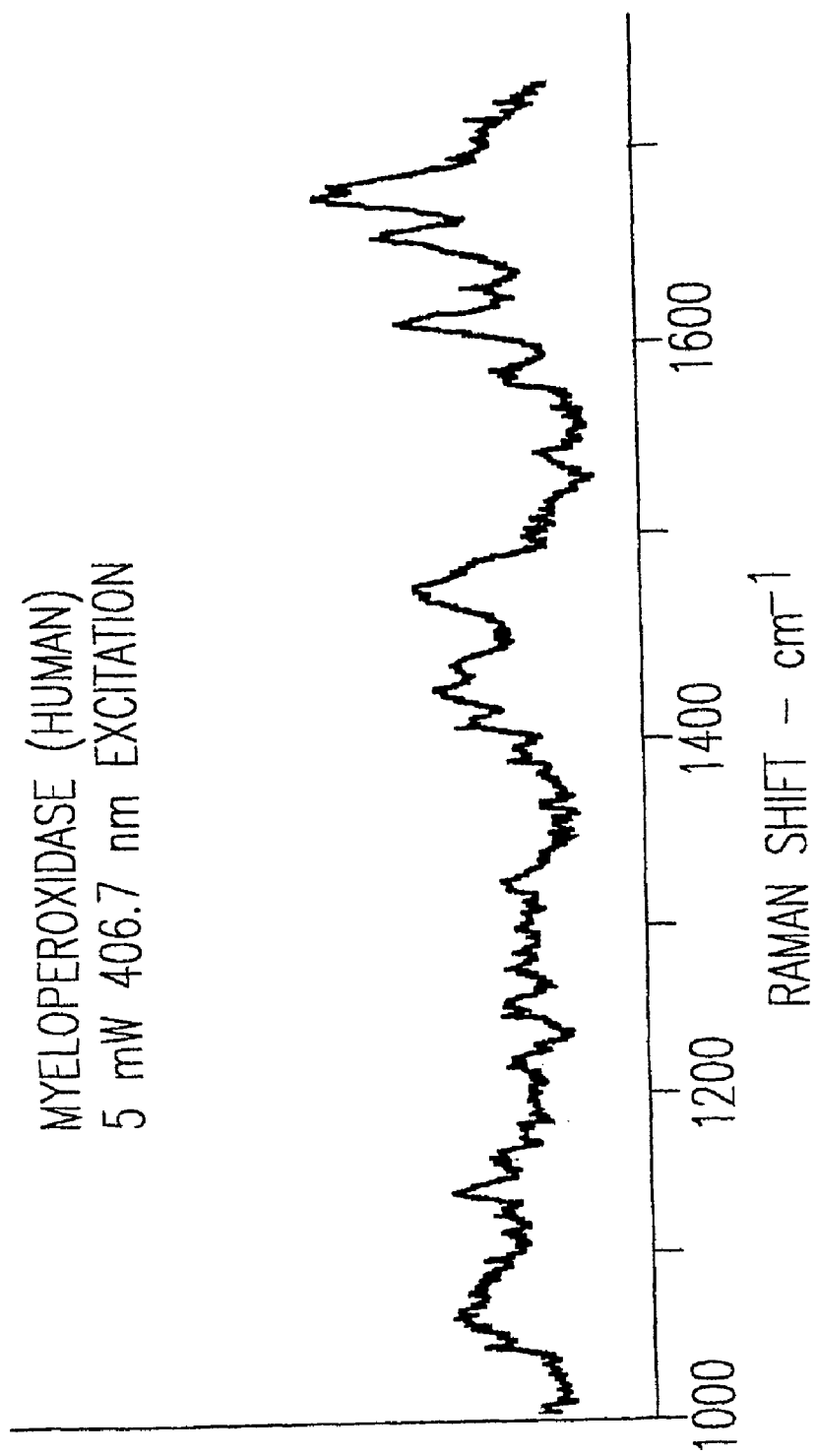
FIG. 23 is a near-UV resonance Raman spectrum of myeloperoxidase.

A resonance Raman spectroscopy spectrum taken for a human is shown for myeloperoxidase (FIG. 23). The ability to detect myeloperoxidase would be helpful in evaluation of wounds and systemic reperfusion injury and sepsis.

Another group of potentially useful markers of preclinical shock secondary to hypovolemia are endogenously produced catecholamines such as epinephrine and norepinephrine and the vasoactive peptides such as angiotensin, vasopressin, endothelin, and adrenomedullin, all of which are known to be significantly elevated in the setting of hypovolemia and other shock states. Jakschik, B. A., Marshall, G. R., Kourik, J. L. Needleman, P., "profile of circulating vasoactive substances in hemorrhagic shock and their pharmacologic manipulation," J Clin Invest, 54(4):842–52 (1974); Lanza, V., Palazzadriano, M., Scardulla, C., Mercadante, S., Valdes, L., Bellanca, G., "Hemodynamics, prolactin and categchloamine levels during hemorrhagic shock in dogs pretreated with ap prolactin inhibitor (bromocriptine)," Pharmacol Res Commun., 19(4):307–18 (1987); Yilmazlar, A., Yilmazlar, T., Ozcan, B., Kutlay, O., "Vasopressin, renin, and adrenocorticotropic hormone levels during the resuscitation of hemorrhagic shock in dogs," J Emerg Med, 18(4):405–8 (2000); Kitajima, T., Tani, K., Yamaguchi, T., Kubota, Y., Okuhira, M., Mizuno, T., et al., "Role of endogenous endothelin in gastric mucosal injury induced by hemorrhagic shock in rats," Digestion, 56(2): 111–6 (1995); Fujioka, S., Ono, Y, Kangawa, K., Okada, K., "Plasma concentration of adrenomedullin is increased in hemorrhagic shock in dogs," Anesth Analg, 88(2):326–8 (1999); Lindner, K. H. Strohmenger, H. U., Ensinger, H., Hetzel, W. D., Ahnefeld, F. W., Georgieff, M., "Stress hormone response during and after cardiopulmonary resuscitation," Anesthesiology, 77(4):662–8 (1992); Lindner, K. H., Haak, T., Keller, A., Bothner, U., Lurie, K. G., "Release of endogenous vasopressors during and after cardiopulmonary resuscitation," Heart, 75(2):145–50 (1996).

Figure 24:
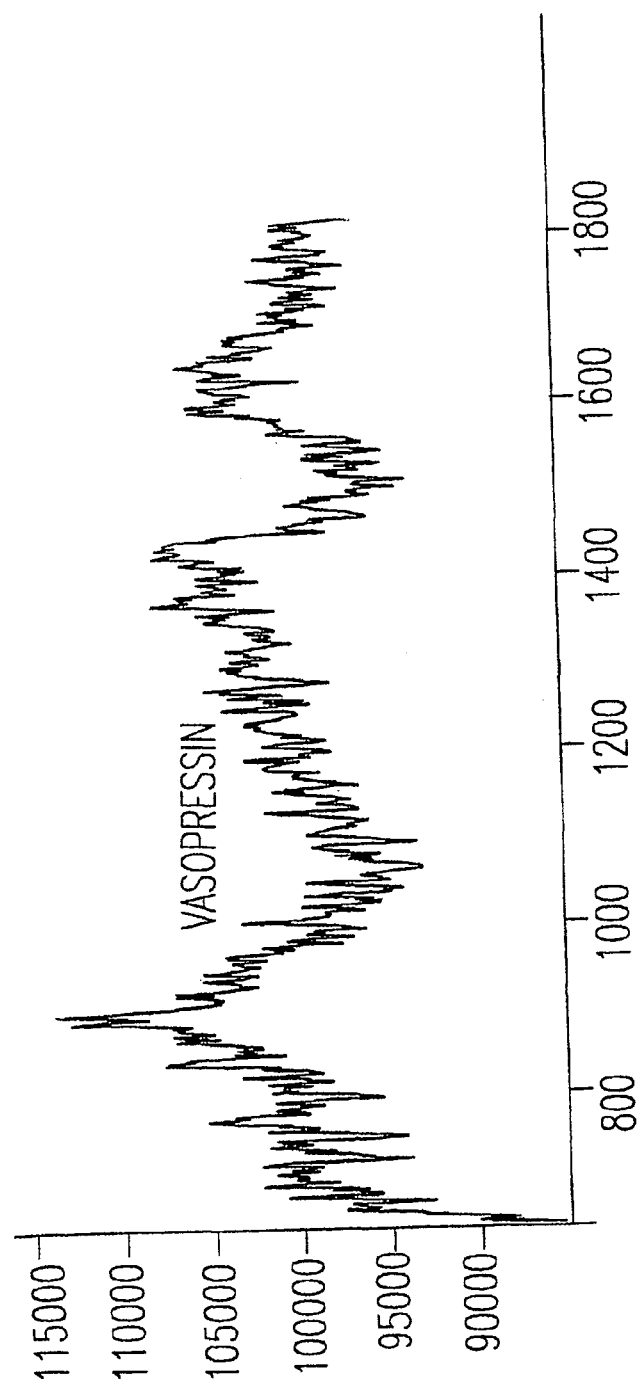
FIG. 24 is a UV resonance Raman spectrum of vasopressin.
Figure 25:
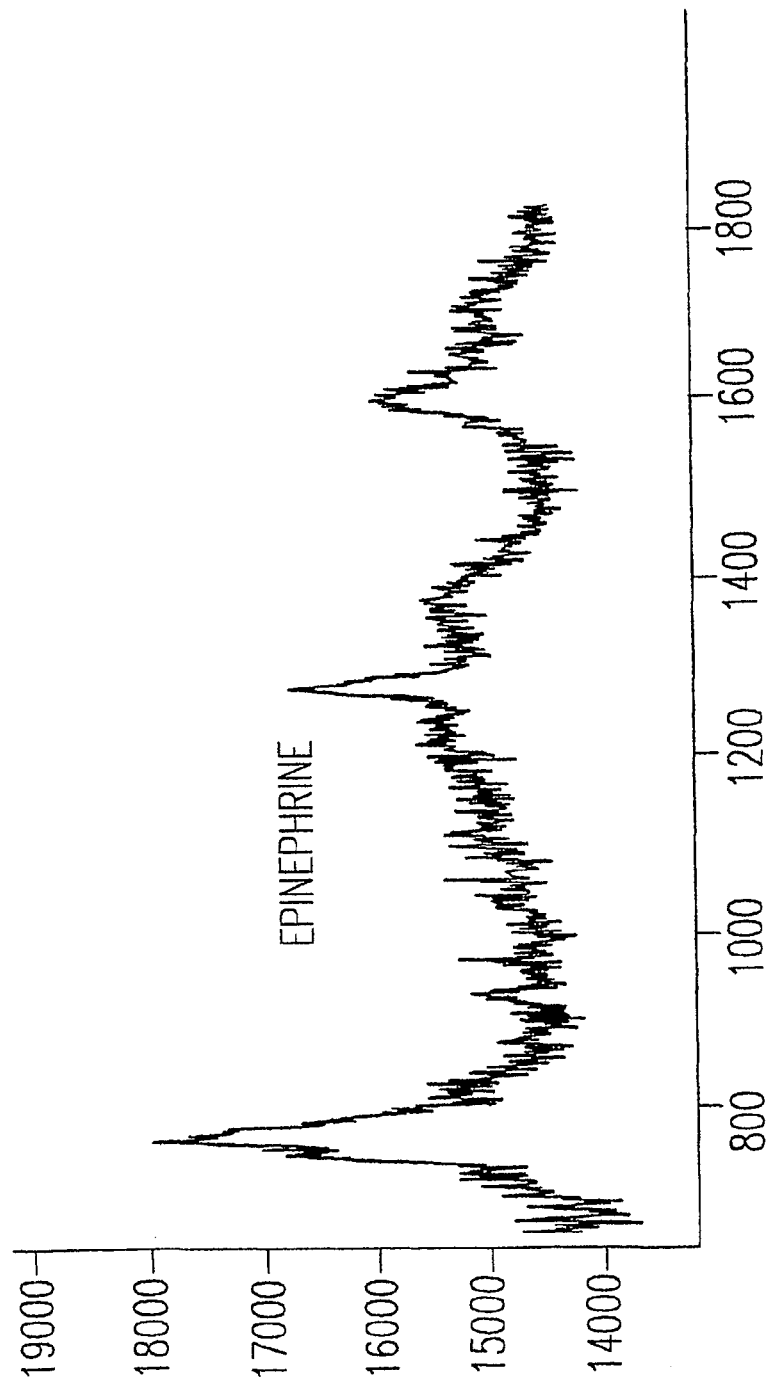
FIG. 25 is a UV resonance Raman spectrum of norepinephrine.

Raman spectra of vasopressin in the UV spectrum at 350 nm is shown at FIG. 24, and for norepinephrine in the same UV spectrum at FIG. 25. Ability to detect, quantitate, and trend these markers can be used with regard to evaluating and treating numerous disease states such as shock, congestive heart failure, pain states, burns, etc. These and other similar mediators can be detected and quantitated using resonance Raman spectroscopy. Schulze, H. G., Greek, L. S., Barbosa, C. J., Blades, M. W., Gorzalka, B. B., Turner, R. F., "Measurement of some small-molecule and peptide neurotransmitters in-vitro using a fiber-optic probe with pulsed ultraviolet resonance Raman spectroscopy," J. Neurosci Methods, 92(1–2):15–24 (1999).

The ability to detect dysoxia and ensure its resolution at the earliest possible time has great value for the triage of ill or injured patients. Therapy and resources can be better allocated and victim's progress better monitored, reducing the incidence of under-resuscitation as well as provision of needless resuscitation. Based on the biphasic relationship of oxygen delivery and consumption of a tissue, the present invention measures hemoglobin saturation in conjunction with NADH as a reflection of the oxygen dependent bioenergetic state of the cell.

Based on experimental results herein, it is seen that near UV excitation can be exploited to simultaneously perform Raman resonance spectroscopy of oxy and deoxyhemoglobin, and surface-subsurface fluorescence of NADH. Also, UV and NIR RRS have been obtained from a number of compounds (including high-energy phosphates PCr, ATP and ADP, NAD, NADH, the glycolytic metabolites pyruvate and lactate, and the excitatory amino acid glutamate) in solid and aqueous states.

From the experimental data set forth above, it may be seen that with the use of combined UV, near UV and NIR Raman spectroscopy, identification and monitoring of a large number of useful target compounds may be accomplished, for detecting and monitoring the presence and severity of hemorrhagic shock and development or resolution of its sequelae such as sepsis. The present inventors have successfully shown that the various compounds discussed above are amenable to detection by UV, near UV and NIR Raman.

It has recently been demonstrated that NIR absorption spectroscopy can be used to determine tissue pH by examining shifts in the broad bands of hemoglobin. This is based on the known fact that histadine residues of hemoglobin are pH sensitive. NIR absorption spectroscopy is being examined to determine hematorcrit in a similar manner. Because pH sensitive shift is observed in all of the oxy and deoxy bands of the resonance Raman spectra and hemoglobin concentration differences in the heights of the bands, it may be concluded (by such techniques as partial least squares) that tissue pH and hematorcit/hemoglobin levels may be determined using resonance Raman spectroscopy.

Of recent importance has been the development of the concept of cytopathic hypoxia as an explanation for the oxygen transport abnormalities, which exist during sepsis. This theory suggests that such inflammatory compounds as tumor necrosis factor and endotoxin damage mitochondria. This damage prevents the mitochondria from utilizing oxygen. Data for studies using NIR absorption spectroscopy appear to support this theory. The combination of near-UV resonance Raman spectroscopy of hemoglobin tissue saturation and NADH fluorescence would help detect this if it existed. In such a setting, tissue saturation would be normal or elevated but NADH fluorescence would be significant. This entity of cytopathic hypoxia may be one factor which confounds the use of other monitoring modalities such as splanchnic tonometry and monitoring of mixed venous oxygen saturation.

Methods and devices according to the invention may be used in various manners, such as to exploit shifts in the spectra of molecules such as hemoglobin and myoglobin to calculate blood and tissue pH as well as detect and determine the actual hemoglobin and myoglobin oxygen saturation. Spectroscopy equipment may be coupled with probe(s) and sensor(s) to construct a device to interrogate the perfusion and metabolic status of individual tissues as well as the organism as a whole, advantageously in a noninvasive or minimally invasive manner. For instance, the invention provides a minimally invasive fiber optic probe or arrays of probes (each probe less than 0.2 mm) which are insertible into a muscle or other tissue bed with a small gauge needle. Resonance Raman spectroscopy in the deep ultraviolet wavelength (less than 270 nm) is used for interstitial fluid analysis (micron level penetration), while longer UV or near UV wavelengths are used for cellular analysis, due to slightly longer wavelengths that could penetrate to levels near 1 mm. Both the deep and near UV wavelengths also may be used with a probe placed on the oral cheek mucosal epithelium. NIR Raman spectroscopy may be used with non-invasive optical fibers placed on the skin or within tissue beds. Surface Raman spectroscopy is used to interrogate standards of detected substances for quantification.

When spectroscopy according to the present invention operates at multiple wavelengths, additional valuable metabolic and humoral targets may be selected for identification and tracking. The one-dimensionality problem of conventional emergency medical measurement technology is avoided. As has been mentioned above, for conventional IR or NIR technology, problems arise because water strongly absorbs IR radiation, and thus presents strong interference to the use of IR absorption spectroscopy in the clinical setting. The present invention is not burdened with such problems because water is a rather weak Raman scatterer. Raman spectroscopy can be used to provide the same vibrational information as the more common NIR absorption spectroscopy with no significant interference from water. In addition, the use of Raman allows one to take advantage of the resonance Raman enhancement effect, plus polarization effects, neither of which have parallels in IR absorption spectroscopy. Thus, a principal advantage of the invention is that Raman spectroscopy does not suffer the same problems with water as normal IR spectroscopy, and, additionally, Raman spectroscopy is not limited to a single wavelength but can use a variety of wavelengths to interrogate molecules of interest at different tissue depths (skin, muscle, etc). Normal and transmission spectroscopy may be used to complement Raman spectroscopy for calibration, determination of tissue depth, and other enhancement of obtained information. Issues such as weakness of signal, potential tissue damage, and interference from fluorescence can be managed.

The ability to target multiple compounds in real-time provided by the present invention is a substantial advantage for detection and treatment of certain disease states and shock states. For example, the ability to monitor levels of catecholamines and vasoactive peptides may prove to be more sensitive of early shock states or states of intractable shock. Elevations of these compounds may indicate the severity of such states as acute sickle cell pain crises. Thus, resuscitation and treatment of such states using markers such as catecholaimnes or vasoactive peptides as endpoints may provide a relatively objective means to determine treatment efficacy.

Another example of methods according to the invention are uses in conjunction with maneuvers such as simple muscle contraction or use of a tourniquet. Monitoring rates of high-energy phosopahte degradation and regeneration or intermediary compound ratios such as lactate-pyruvate or NAD-NADH in disease states may provide relatively sensitive information concerning the state of the microvasculature.

Outpatient applications also are provided. Depending on the sensitivity of the device, the technology of the invention may be used in the outpatient setting for determination of various target compounds such as hemoglobin. The device may be used to diagnose certain precancerous or cancerous lesions (such as skin melanoma, etc.) in vivo. Point of care or continuous real-time tissue monitoring is provided with the inventive method and its components.

Because probes may be relatively small, patients may be continuously interrogated for the appearance of abnormal tissue markers specific for a suspected disease state. Examples of such markers are cardiac biomarkers such as troponin or myocardial fatty acid binding protein, GI markers of ischemia scuh as D-lactate and intestinal fatty acid-binding protein, and cerebral markers such as neuronal enolase.

Combining resonance Raman spectroscopy of tissue hemoglobin saturation and NADH fluorescence of the same region provides for detecting ultra-early perfusion deficits and determining adequacy of resuscitation. The present invention provides at least the following advantages: 1) little or no tissue contact (point and click technology); 2) rapid acquisition (such as acquisition times on the order of 1 second); 3) data (tissue saturation and point of critical oxygen delivery) that is not confounded by hypo or hypercarbia; 4) differentiation of sepsis (cytopathic hypoxia) from flow dependent dysoxia; 5) true data from mucosa (oral or other points in the GI or GU tract); 6) pH and hemaglobin (on a par with NIR absorption technology); and 7) other important markers of tissue injury such as myeloperoxidase, xanthine oxidase, vasocative substances, etc.

The present invention may be applied to known markers and also to markers as newly reported, because of the nature of resonance Raman spectroscopy. As a new marker (such as procalcitonin, etc.) is reported, the present invention provides for its study by resonance Raman spectroscopy.

The inventive methods and devices may be used for evaluation of any general shock state (trauma, cardiogenic, septic). Applications include hypoxic-hypoxia, hemorrhagic shock, cardiogenic shock, septic shock, and isolated organ ischemia (including wounds).

The inventive methods and devices may be used to evaluate the oxygen status of any organ during surgery (e.g., the heart during cardiopulmonary bypass surgery, the brain during neurosurgery, and various organs during transplant); to evaluate donor organs prior to transplant; to include in devices such as pacemakers to interrogate areas of myocardium at risk of injury; to evaluate a patient with congestive heart failure (such as at the hospital, office, home, etc.) to determine symptom etiology (such as fluid overload versus deterioration in heart function); to determine if a patient requires blood transfusion; to care for wounds.

The invention fills the current void of no universally accepted way of determining when a patient requires blood transfusion. Because each patient may have a different requirement based on past medical history and the current event, the invention is highly advantageous in allowing repetitive noninvasive measures of a sensitive tissue.

The invention benefits wound care (chronic and acute), by providing information about the oxygenation status of wounds. Care of chronic wounds is improved by the present invention providing the ability to determine oxygenation status of wounds. The use of near-UV resonance Raman spectroscopy determines tissue oxygen saturation at multiple points within the wound (within seconds) with tissue contact being unnecessary. In conjunction with the Raman spectroscopy, NADH fluorescence may be used to determine if the wound is becoming necrotic. The wound may be sampled for injurious substances interfering with wound-healing, such as myeloperoxidase.

The methods and products of the present invention have civilian and military uses. Using UV, near UV or NIR Raman spectroscopy according to the present invention provides for real-time monitoring of a broad range of valuable markers. An operator (such as a combat medic) may use a portable probe according to the invention, with the probe being pluggable into a hand held UV-NIR Raman spectrometer (such as a device the size of a hand held palm PC device). The Raman spectrometer before use on a patient may be programmed to perform V, near UV and NIR Raman spectroscopy for the markers of interest and to report them in a manner readily interpretable to indicate the presence and degree of shock. In the case of a combat medic using such a portable probe that plugs into a Raman spectrometer, the medic may then institute or order appropriate therapy while instrumenting and interrogating the next soldier using the same hand held spectrometer. In this manner, the medic can move back and forth between patients to determine the effect of the instituted therapy and to make triage decisions. When a marker or a combination of markers indicates intractable shock, an appropriate triage decision may be more readily reached than without the measurement information according to the present invention, and thus other more salvageable patients may be more likely to have access to resources and have increased chances of survival.

Data collected according to the present invention may be stored and/or transmitted. For example, data collected by a hand held device (such as a combat medic device) may be transmitted to a remote data bank. As the patient is transported, medics and physicians taking over care may use their own devices (which may be hand held devices) to hook into the previously implanted fiber optic probe. Data measured during a new hook-up may be compared to data previously collected on the patient (such as data transmitted earlier from the field). New or additional probes optionally may be placed during surgery. The same devices, once placed, may be maintained in place and used to continuously interrogate tissue to monitor the efficacy of ongoing resuscitative efforts and to detect the development of post-hemorrhagic shock and surgical sequelae such as early sepsis. Multiple tissues beds may be interrogated, especially by using small, disposable probes.

While an operator has been referred to hereinabove, it will be appreciated that the inventive methods do not necessarily require a human operator, and that the invention may include partly and entirely automatic, such as computer-assisted, methods and devices. Such automatic and semi-automatic methods and devices may include those in which, upon measurement of ratios or amounts in a certain pre-determined adverse range, pre-formulated reactive therapies are applied. The invention provides for an optional computer system, such as a computer system comprising a database of stored baseline Raman spectroscopy and/or fluorescence spectroscopy profiles and a means to store patient Raman spectroscopy and/or fluorescence spectroscopy profiles. Such a computer system preferably includes a computing system for comparing patient profiles to baseline profiles.

While the invention has been described in terms of its preferred embodiments, those skilled in the art will recognize that the invention can be practiced with modification within the spirit and scope of the appended claims.

We claim:

1. A tissue analysis method, comprising:
   interrogating a biological tissue with Raman spectroscopy and fluorescence spectroscopy to obtain spectroscopy results; analyzing the obtained spectroscopy results for at least one mediator or marker associated with a shock state.

2. The method of claim 1, wherein the tissue interrogating is noninvasive.

3. The method of claim 1, wherein the tissue is in vivo and in situ.

4. The method of claim 1, wherein the tissue is removed from a patient before the tissue interrogation.

5. The method of claim 1, including measuring NADH presence and/or accumulation by fluorescence spectroscopy.

6. The method of claim 1, including measuring tissue hemoglobin oxygen saturation by Raman spectroscopy and measuring NADH presence and/or accumulation by fluorescence spectroscopy.

7. The method of claim 1, including determining whether the tissue has insufficient oxygen delivery to meet metabolic demands of the tissue while simultaneously determining whether mitochondrial dysfunction or injury exists.

8. The method of claim 1, including measuring myoglobin oxygenation saturation.

9. The method of claim 1, including determining cytochrome oxidase redox status.

10. The method of claim 1, including determining absolute concentration of hemoglobin in the tissue.

11. The method of claim 1, including determining pH of the tissue.

12. The method of claim 1, including intermittently or continuously interrogating the tissue of a patient.

13. The method of claim 1, including determining tissue viability.

14. The method of claim 1, including diagnosing shock.

15. A tissue analysis method, comprising:
    interrogating a biological tissue with Raman spectroscopy and fluorescence spectroscopy to obtain spectroscopy results, including:
    measuring tissue hemoglobin oxygen saturation including amount of oxyhemoglobin and deoxyhemoglobin by Raman spectroscopy; and/or
    measuring tissue hemoglobin oxygen saturation by Raman spectroscopy and measuring NADH presence and/or accumulation by fluorescence spectroscopy; and/or
    determining whether the tissue has insufficient oxygen delivery to meet metabolic demands of the tissue while simultaneously determining whether mitochondrial dysfunction or injury exists.

16. The tissue analysis method of claim 15, wherein the obtained spectroscopy results are for at least one mediator or marker associated with a shock state and/or tissue injury.

17. The method of claim 16, wherein the obtained spectroscopy results are for presence and/or proportions for the at least one shock state and/or tissue injury mediator or marker.

18. The method of claim 16 including determining the concentration of at least one mediator or marker.

19. The method of claim 18, including determining absolute concentration.

20. The method of claim 18, including determining relative concentration.

21. The method of claim 16 including determining the presence of at least one mediator or marker.

22. The method of claim 16, wherein the obtained spectroscopy results are selected from the group consisting of at least one mediator associated with a shock state, tissue injury or tissue ischemia, inflammation or immune dysfunction, and at least one marker of tissue perfusion or injury.

23. The method of claim 22, wherein the marker may be within intracellular, interstitial or intravascular space or within exhaled air from a patient.

24. The method of claim 22, wherein the marker is selected from the group consisting of lactate, pyruvate, ATP, Pcr, AMP, ADP, Pi, NAD, NADH, albumin, endotoxin, exotoxin, microbes, cytokines-chemokines, procalcitonin, hormones, myeloperoxidase, elastase, xanthine oxidase, xanthine dehydrogenase, fatty acid binding proteins, catecholamines and vasoactive peptides.

25. The method of claim 22, wherein the marker or mediator is a metabolic or pro or anti-inflammatory marker or mediator.

26. The method of claim 16, including monitoring for appearance of one or more tissue markers specific for a specific disease state.

27. The method of claim 16, including diagnosing tissue injury, tissue inflammation or tissue immune dysfunction.

28. The method of claim 15, including diagnosing and/or following progression or resolution of shock states and/or tissue injury, and/or tissue ischemia.

29. The method of claim 28, wherein the tissue injury includes inflammatory or immune dysfunction.

30. The method of claim 15, including determining absolute concentration of hemoglobin in the tissue.

31. The method of claim 15, including determining pH of the tissue.

32. The method of claim 15, including continuously interrogating the patient for appearance of abnormal tissue markers specific for a suspected disease state.

33. The method of claim 32, wherein the markers are cardiac biomarkers, GI markers, cerebral markers, skin markers, lung markers, blood markers, and/or eye markers.

34. The tissue analysis method of claim 15, including measuring tissue hemoglobin oxygen saturation including amount of oxyhemoglobin and deoxyhemoglobin by Raman spectroscopy.

35. The tissue analysis method of claim 15, including measuring tissue hemoglobin oxygen saturation by Rama spectroscopy and measuring NADH presence and/or accumulation by fluorscence spectroscopy.

36. The tissue analysis method of claim 15, including determining whether the tissue has insufficient oxygen delivery to meet metabolic mends of the tissue while simultaneously determining whether mitochondrial dysfunction or injury exists.

37. A method of diagnosing shock, comprising:
   (A) for a target molecule population, taking a sample Raman spectroscopy, and/or fluorescence spectroscopy, profile for a patient;
   (B) comparing the sample spectroscopy profile with a pre-established Raman spectroscopy and/or fluorescence spectroscopy profile for the target molecule population under baseline conditions; and,
   (C) diagnosing shock based on results of the comparing step.

38. The method of claim 37, wherein the method is non-invasive.

39. The method of claim 37, wherein the target molecule population comprises oxygenated hemoglobin, deoxygenated hemoglobin and/or NADH.

40. The method of claim 37, wherein the profiles are of relative amounts.

41. The method of claim 40, including operating an electromagnetic radiation generator at a range of selectable wavelengths from about 270 mm to about 30,000 nm.

42. The method of claim 37, wherein the profiles are of absolute amounts.

43. The method of claim 37, including taking the profiles by Raman spectroscopy.

44. The method of claim 43, including signal enhancement at a resonant frequency for a target molecule of the target molecule population.

45. The method of claim 37, including monitoring a specific tissue bed in the patient.

46. The method of claim 45, wherein the specific tissue bed is a brain, heart, lung, liver, eye, intestines, stomach, pancreas, kidney, bladder, urethra, skin, nailbed, cervix, uterus, oropharynx, nasopharynx, eosphagus or blood.

47. The method of claim 37, including calculating pH of blood and/or tissue.

48. The method of claim 37, including minimally invasively probing the patient by a fiber optic probe or probe array inserted into a tissue bed.

49. The method of claim 48, wherein the probe or probe array is inserted into a muscle.

50. The method of claim 37, including analysis of interstitial fluid.

51. The method of claim 32, including resonance Raman spectroscopy at 390 to 420 nm wavelength.

52. The method of claim 51, wherein the sample profile is taken from a tissue or a space in a body.

53. The method of claim 51, wherein the sample profile is taken from a tissue or a space out of the body.

54. The method of claim 37, including cellular analysis.

55. The method of claim 37, including placing a probe on or near any mucosal or epithelial covered surface of a body or an organ.

56. The method of claim 37, including simultaneously performing fluorescence spectroscopy probing of NADH while performing Raman spectroscopy.

57. The method of claim 37, wherein spectroscopy is performed for multiple wavelengths.

58. A method of diagnosing shock, tissue ischemia, tissue injury, tissue inflammation, or tissue immune dysfunction, comprising:
   (A) for a target molecule population, taking a sample Raman spectroscopy, and/or fluorescence spectroscopy, profile for a patient;
   (B) comparing the sample spectroscopy profile with a pre-established Raman spectroscopy and/or fluorescence spectroscopy profile for the target molecule population under baseline conditions, wherein the profiles are of relative amounts of NAD/NADH; lactate/pyruvate; Pcr-ATP; ATP-ADP; Pcr-Pi; oxidized cytochrome oxidase to reduced cytochrome oxidase, and/or oxyhemoglobin with deoxyhemoglobin.

59. A method of diagnosing shock, tissue ischemia, tissue injury, tissue inflammation, or tissue immune dysfunction, comprising:
   (A) for a target molecule population, taking a sample Raman spectroscopy, and/or fluorescence spectroscopy, profile for a patient;
   (B) comparing the sample spectroscopy profile with a pre-established Raman spectroscopy and/or fluorescence spectroscopy profile for the target molecule population under baseline conditions, including detecting exhaled markers or mediators of organ injury.

60. The method of claim 59, wherein exhaled markers or mediators of lung injury are detected.

61. The method of claim 59, wherein a detector is placed at the airway of the patient.

62. The method of claim 59, wherein the exhaled markers indicate organ injury.

63. The method of claim 59, wherein the exhaled markers or mediators are isoprostanes and/or myeloperoxidase.

64. A method of diagnosing abnormalities in vivo and in situ, comprising:
   (A) for a target molecule population, taking a sample Raman spectroscopy and/or fluorescence spectroscopy profile for a patient;
   (B) comparing the sample Raman spectroscopy or fluorescence spectroscopy profile with a pre-established Raman spectroscopy or fluorescence spectroscopy profile for the target molecule population under baseline conditions;
   (C) using differences identified in said comparing step to identify an abnormality associated with a shock state.

65. The method of claim 64, including, while taking the Raman spectroscopy profile, also performing fluorescence spectroscopy measurement on the patient.

66. A computer system comprising:
   a database of stored baseline Raman spectroscopy and/or fluorescence spectroscopy profiles and
   a means to store patient Raman spectroscopy and/or fluorescence spectroscopy profiles;
including a computing system for comparing patient profiles to baseline profiles with regard to a shock state.

67. A biological material analysis method, comprising:
   interrogating a biological material with Raman spectroscopy and fluorescence spectroscopy to obtain spectroscopy results;
analyzing the obtained spectroscopy results for at least one mediator or marker associated with a shock state.

68. The biological material analysis method of claim 67, wherein the biological material is bodily fluid.

69. The biological material analysis method of claim 67, wherein the biological material is tissue.

70. The method of claim 67, wherein the marker is contained in a biological material selected from the group consisting of urine, saliva, wound exudates, vitreous humor, aqueous humor, tissue exudate, gastric contents, and fecal matter.

* * * * *

UNITED STATES PATENT AND TRADEMARK OFFICE
CERTIFICATE OF CORRECTION

| | | |
|---|---|---|
| PATENT NO. | : 7,113,814 B2 | Page 1 of 1 |
| APPLICATION NO. | : 10/332613 | |
| DATED | : September 26, 2006 | |
| INVENTOR(S) | : Kevin R. Ward et al. | |

It is certified that error appears in the above-identified patent and that said Letters Patent is hereby corrected as shown below:

In the Specification

At Column 1, line 5, please insert the following:

--STATEMENT OF GOVERNMENT INTEREST

This invention was made with government support under contract number GM57042 awarded by the National Institutes of Health. The government has certain rights in the invention.--

Signed and Sealed this
Twenty-third Day of December, 2014

Michelle K. Lee
*Deputy Director of the United States Patent and Trademark Office*